United States Patent
Wilger et al.

(10) Patent No.: US 10,231,858 B2
(45) Date of Patent: Mar. 19, 2019

(54) DELIVERY SYSTEM FOR PRELOADED FENESTRATED DEVICE

(71) Applicant: Cook Medical Technologies LLC, Bloomington, IN (US)

(72) Inventors: Kevin Wilger, Fuquay Varina, NC (US); Jarin Kratzberg, Lafayette, IN (US); Rick Hadley, Otterbein, IN (US); Siddharth Vad, Bloomington, IN (US); Brandon Davis, West Lafayette, IN (US); Ryan Bradway, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 344 days.

(21) Appl. No.: 14/968,318

(22) Filed: Dec. 14, 2015

(65) Prior Publication Data

US 2016/0175132 A1    Jun. 23, 2016

Related U.S. Application Data

(60) Provisional application No. 62/095,492, filed on Dec. 22, 2014, provisional application No. 62/235,247, filed on Sep. 30, 2015.

(51) Int. Cl.
*A61F 2/95* (2013.01)
*A61F 2/97* (2013.01)
*A61F 2/962* (2013.01)

(52) U.S. Cl.
CPC ............... *A61F 2/962* (2013.01); *A61F 2/97* (2013.01); *A61F 2002/9517* (2013.01)

(58) Field of Classification Search
CPC .... A61F 2/95; A61F 2/954; A61F 2/97; A61F 2002/9517; A61F 2/958; A61F 2/962–2/966; A61F 2002/9583; A61F 2002/9665; A61M 25/0071; A61M 2025/0681
See application file for complete search history.

(56) References Cited

U.S. PATENT DOCUMENTS

| 4,631,059 A | 12/1986 | Wolvek et al. |
| 4,697,573 A | 10/1987 | Schiff |

(Continued)

FOREIGN PATENT DOCUMENTS

| EP | 2 626 045 A1 | 8/2013 |
| WO | WO 2007/059280 A1 | 5/2007 |
| WO | WO 2007/142962 A2 | 12/2007 |

OTHER PUBLICATIONS

Extended European Search Report from corresponding European Application No. 152755270.5, 5pp., dated May 2, 2016.

(Continued)

*Primary Examiner* — Katrina M Stransky
*Assistant Examiner* — Lindsey Bachman
(74) *Attorney, Agent, or Firm* — Brinks Gilson & Lione

(57) ABSTRACT

A pre-loaded stent graft delivery device having a guide wire catheter and a handle including a multi-port manifold with access ports, where an access sheath extends from each access port. A sheath is disposed coaxially around the guide wire catheter and includes two splits that enable the retraction of the sheath while the access sheaths are disposed within the respective access port of the manifold.

20 Claims, 22 Drawing Sheets

(56) References Cited

U.S. PATENT DOCUMENTS

| | | | |
|---|---|---|---|
| 5,261,887 A | 11/1993 | Walker | |
| 7,814,662 B2 | 10/2010 | O'Neal | |
| 2007/0282419 A1* | 12/2007 | Hilaire | A61F 2/856 623/1.11 |
| 2007/0299499 A1* | 12/2007 | Hartley | A61F 2/962 623/1.11 |
| 2008/0319524 A1* | 12/2008 | Yachia | A61F 2/95 623/1.11 |
| 2011/0054594 A1* | 3/2011 | Mayberry | A61F 2/07 623/1.34 |
| 2011/0282425 A1* | 11/2011 | Dwork | A61F 2/95 623/1.11 |
| 2012/0172887 A1 | 7/2012 | Hatfield | |
| 2014/0121753 A1 | 5/2014 | Dorn et al. | |

OTHER PUBLICATIONS

Extended European Search Report from corresponding European Application No. EP 17152719.5-1651, 6pp., dated Feb. 22, 2017.

\* cited by examiner

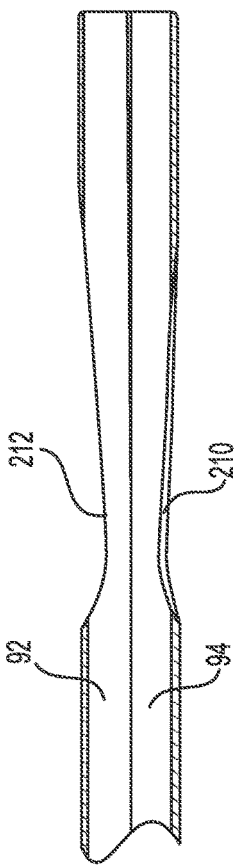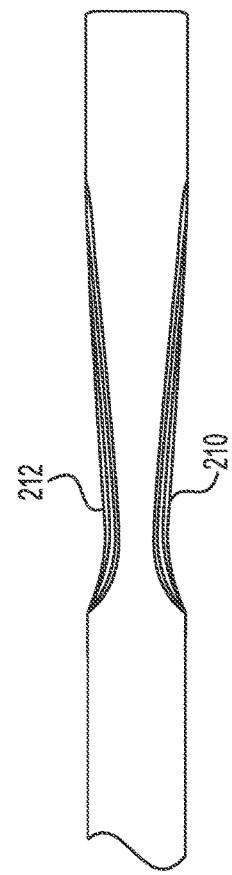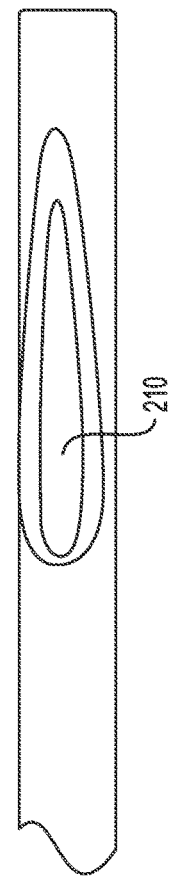
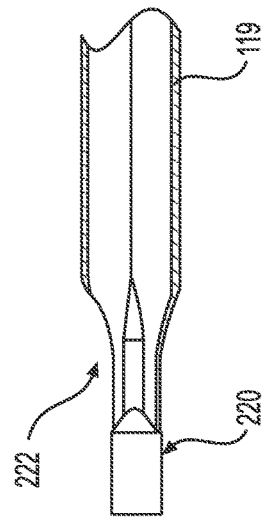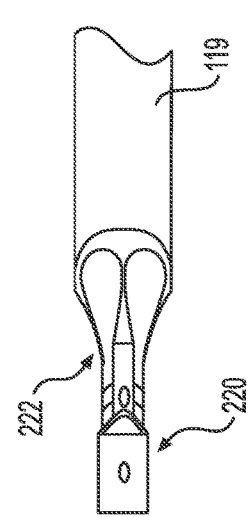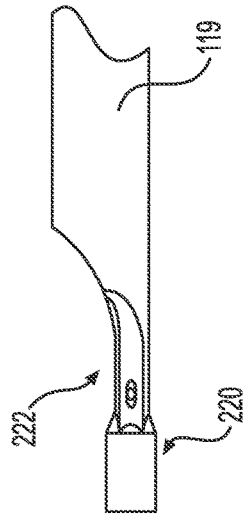
FIG. 11A  FIG. 11B  FIG. 11C

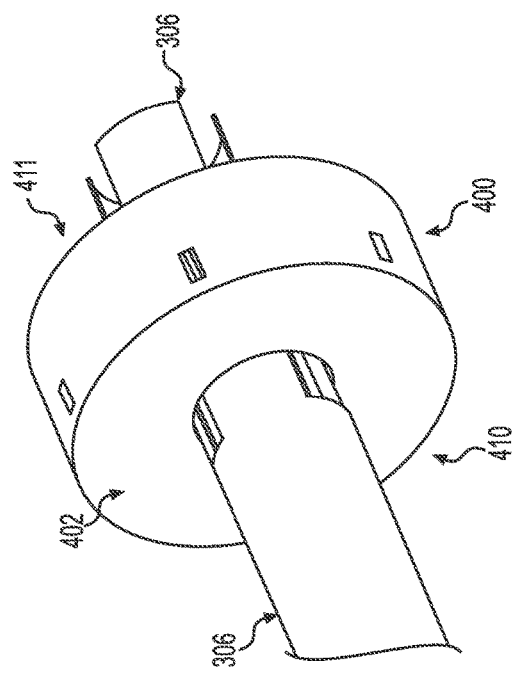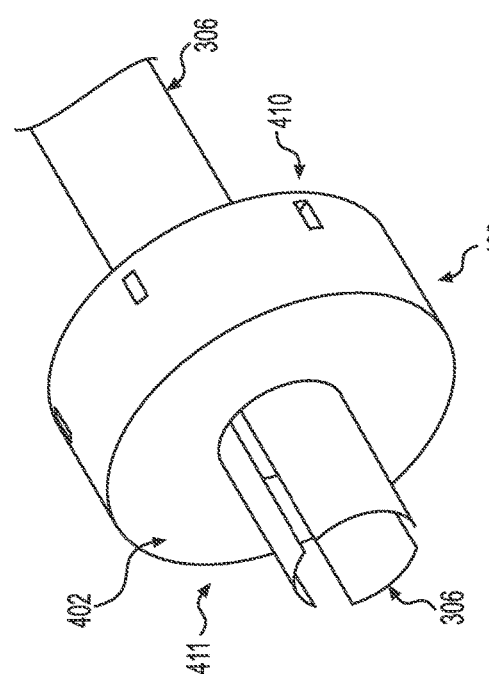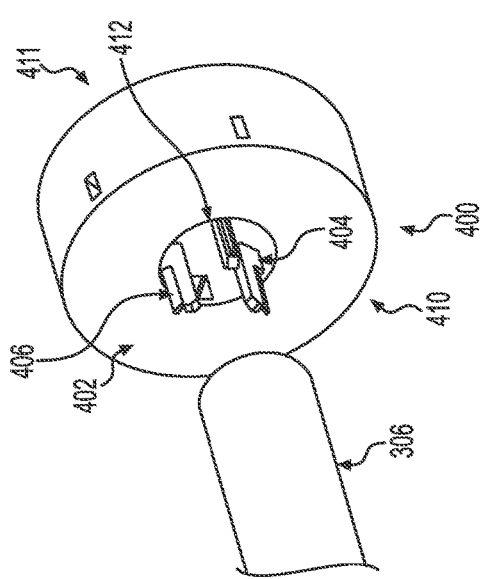

DELIVERY SYSTEM FOR PRELOADED FENESTRATED DEVICE

PRIORITY CLAIM

This application claims the benefit of priority of U.S. Provisional Application Ser. No. 62/095,492, entitled "Delivery System for Preloaded Fenestrated Device," filed Dec. 22, 2014, and U.S. Provisional Application Ser. No. 62/235,247, entitled "Delivery System for Preloaded Fenestrated Device," filed Sep. 30, 2015, the disclosures of which are hereby incorporated by reference in their entirety.

TECHNICAL FIELD

This invention relates to a medical device and more particularly to a device for introduction or delivery of a stent graft into the vasculature of a patient.

BACKGROUND OF THE INVENTION

It is known to introduce endovascular stent grafts into the vasculature of a patient to bridge an aneurism or damaged portion of the wall of the vasculature. Problems can occur, however, where the damage to the vasculature includes or is adjacent to a branch vessel from a main artery because the branch vessel may be occluded by the stent graft and cause permanent damage to the patient. Examples of such branch vessels are the renal and the mesenteric arteries extending from the aorta.

Fenestrations in a stent graft have been proposed to allow access to a branch vessel from a main stent graft but it is often necessary to provide a side branch graft to maintain access into the branch vessel. Catheterisation of such a branch vessel from a delivery device through the fenestration enables deployment of a covered stent or uncovered stent into the branch vessel. This invention provides an improved apparatus for catheterisation and deployment of side branch grafts.

SUMMARY OF THE INVENTION

In one embodiment of the present invention, a pre-loaded stent graft delivery device includes a guide wire catheter having a guide wire lumen therethrough, a handle assembly at a distal end of the guide wire catheter, the handle assembly including a manifold, where the manifold comprises two side ports and an through bore, the two side ports extending distally from the through bore, a nose cone dilator at the proximal end of the guide wire catheter, a pusher catheter extending from the manifold towards the nose cone dilator, where pusher catheter includes at least one lumen therethrough where the guide wire catheter extends through the lumen within the pusher catheter, a access sheath disposed within each of the two side ports of the manifold, and a sheath disposed coaxially over the pusher catheter, where the sheath has at least two longitudinal splits formed along a portion of the length of the sheath, where each split is aligned with each of the access sheaths such that the sheath can be at least partially retracted over the access sheaths.

In another embodiment of the present invention, the pre-loaded stent graft delivery device includes a guide wire catheter having a guide wire lumen therethrough, a handle assembly at a distal end of the guide wire catheter, the handle assembly including a manifold, where the manifold comprises two side ports and an through bore, the two side ports extending distally from the through bore, a handle forming part of the handle assembly, the handle rotatable about the guide wire catheter, a nose cone dilator at the proximal end of the guide wire catheter, a pusher catheter extending from the manifold towards the nose cone dilator, the pusher catheter comprising at least one lumen therethrough where the guide wire catheter extends through the lumen within the pusher catheter, a access sheath disposed within each of the two side ports of the manifold, and a sheath disposed coaxially over the pusher catheter having a distal end that is rotatably coupled to the handle, where the sheath has at least two longitudinal splits formed along a portion of the length of the sheath, where each split is aligned with each of the access sheaths such that the sheath can be at least partially retracted over the access sheaths.

In one embodiment of the present invention, a pre-loaded stent graft delivery device includes a manifold with three access ports and a central aperture, the three access ports extending distally from the central aperture; three access sheaths, where each access sheath is disposed within a corresponding access port of the manifold; a tri-lumen catheter extending proximally from the manifold, the tri-lumen catheter comprising three auxiliary lumens therethrough where each access sheath extends through a corresponding auxiliary lumen within the tri-lumen catheter; and a sheath disposed coaxially over the tri-lumen catheter, where the sheath has at least three longitudinal splits formed along a portion of the length of the sheath, where each split is aligned with a corresponding access sheath such that the sheath can be at least partially retracted over the access sheaths.

BRIEF DESCRIPTION OF THE DRAWINGS

FIGS. 11A to 11D show various views of the pusher catheter of the embodiment of the stent graft delivery device shown in FIG. 1.

FIGS. 23A, 23B, and 23C show perspective views of a cutter and a sheath suitable for the embodiment of the stent graft delivery device shown in FIG. 1.

DETAILED DESCRIPTION OF THE DRAWINGS AND THE PRESENTLY PREFERRED EMBODIMENTS

Throughout this specification the term distal with respect to a portion of the aorta, a delivery device or a prosthesis means the end of the aorta, delivery device or prosthesis further away in the direction of blood flow away from the heart and the term proximal means the portion of the aorta, delivery device or end of the prosthesis nearer to the heart. When applied to other vessels similar terms such as caudal and cranial should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

Figure 1:
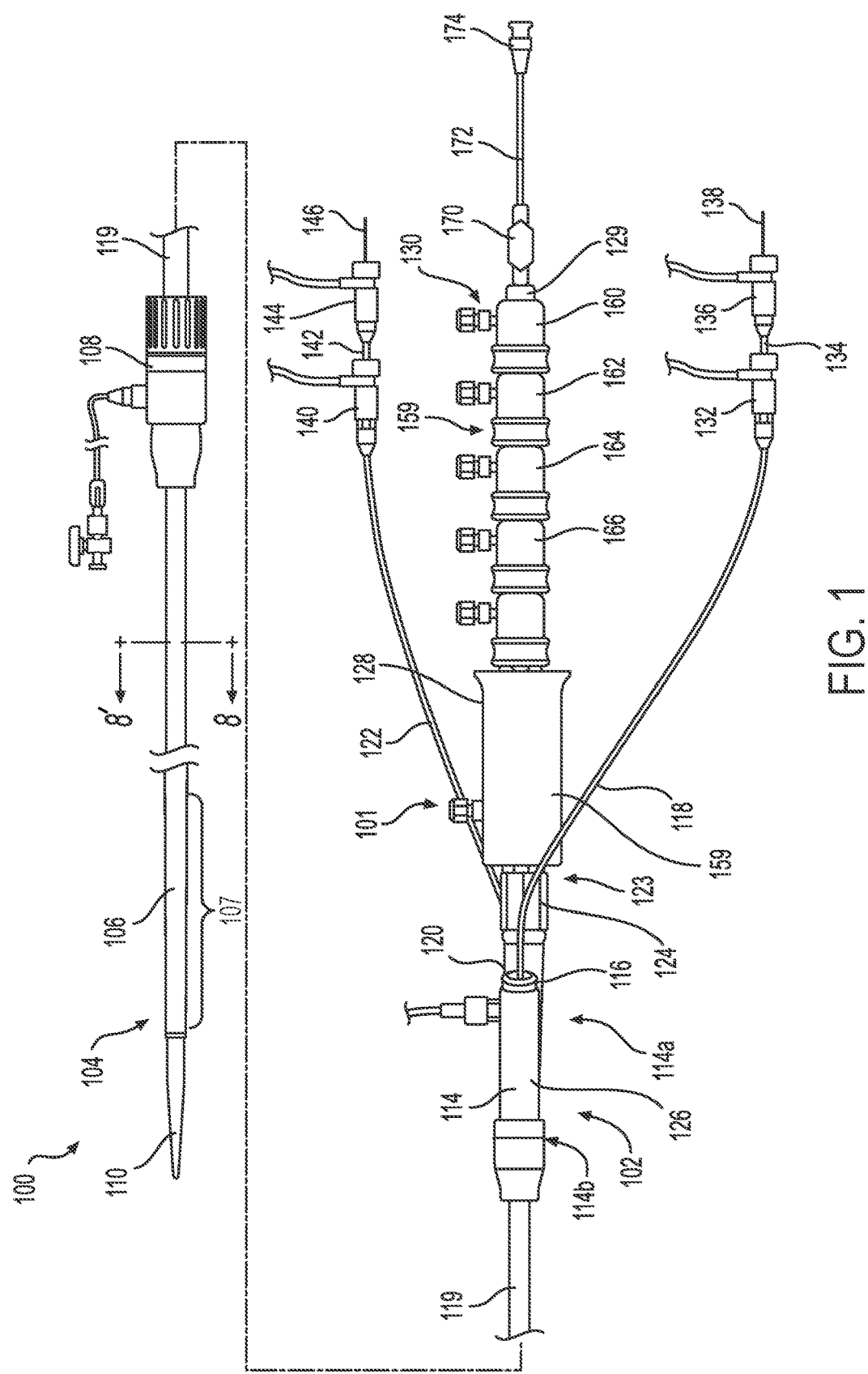
FIG. 1 shows an embodiment of a pre-loaded stent graft delivery device according to the present invention.
Figure 2:
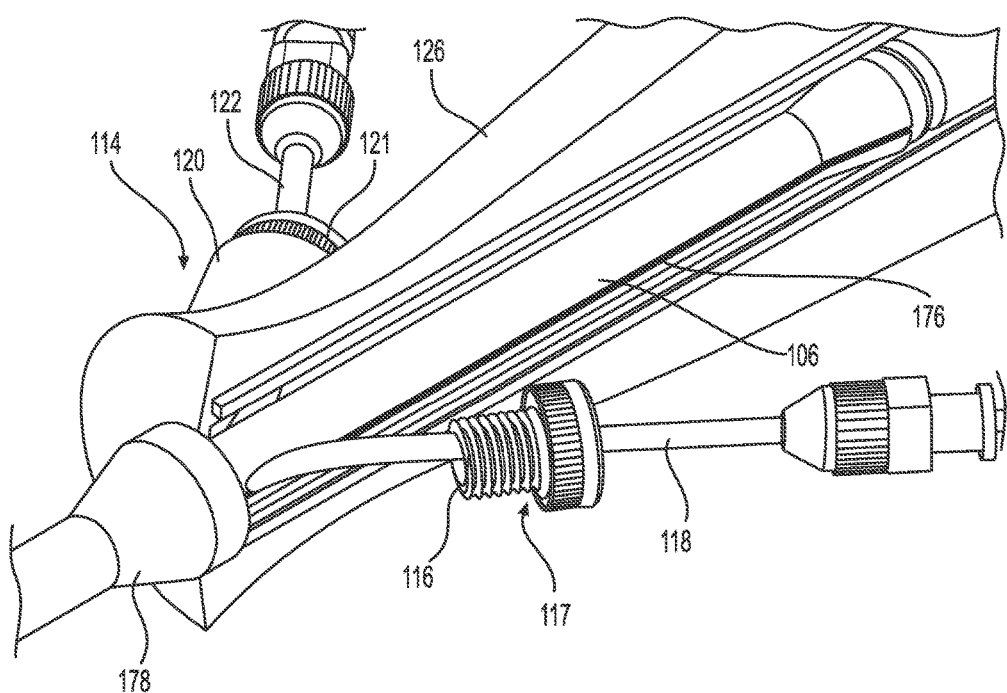
FIG. 2 shows a partial cross-sectional view of a handle portion of the embodiment of the stent graft delivery device of FIG. 1.

As shown in FIG. 1, the delivery device 100 comprises a handle 101 and manifold assembly 102 and introduction portion 104 intended to be deployed into the patient by the known Seldinger method. More specifically the introduction portion 104 includes a sheath 106 extending from a sheath hub 108 to a nose cone dilator 110. A secondary sheath 178, shown in FIG. 2, is disposed about the sheath 106. A stent graft 131 is retained within the outer sheath 106 in the region 107 just distal of the nose cone dilator 110.

The sheath hub 108 is positioned over a tri-lumen catheter 119 which extends from and is connected into a manifold 114 as is discussed in more detail below. The manifold 114 has a proximal end 114b into which is affixed the tri-lumen catheter 119 and two access ports 116, 120 at its distal end 114a.

Figure 3:
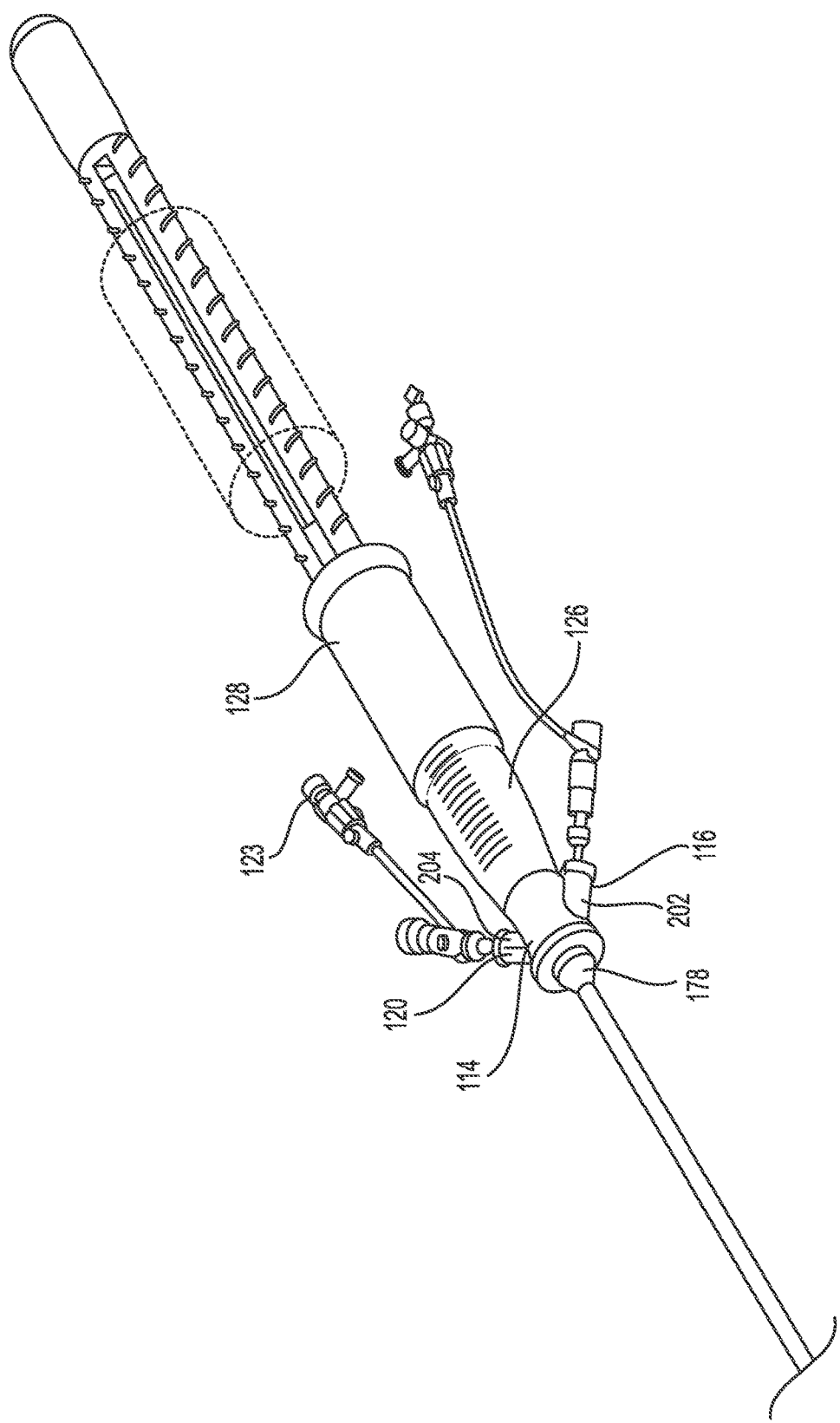
FIG. 3 is a prospective view of the distal portion of the embodiment of the stent graft delivery device of FIG. 1.

As shown in FIGS. 2 and 3, a handle assembly 123 is provided and comprises a front handle 126 and a back handle 128 as shown in FIG. 3. The manifold 114 forms part of the front handle 126. It is understood that the manifold 114 can be separate from the front handle 126 and can be disposed either proximal or distal to the front handle 126. As further shown in FIG. 2, the manifold 114 includes an access port 116 for a first access sheath 118 that extends from the manifold portion 114 of the front handle 126. Access port 120 is provided for a second access sheath 122. The access ports 116, 118 include haemostatic seals 117, 121.

The first access sheath 118 extends to a haemostatic seal 132 through which extends a dilator 134. On the dilator 134 is a dilator haemostatic seal 136 through which extends an indwelling guide wire 138. Likewise, the second access sheath 122 extends to a haemostatic seal 140 through which extends a dilator 142. On the dilator 142 is a dilator haemostatic seal 144 through which extends an indwelling guide wire 146.

Turning back to the handle assembly 123, as shown in FIG. 3, the back handle 128 is disposed distal to the front handle 126. As will be discussed in greater detail below, the back handle 128 can rotate with respect to the front handle 126 and manifold 114. In one embodiment, a trigger wire release mechanism 159 is adjacent to the handle assembly 123. As shown in FIGS. 1 and 3, the handle assembly 123 includes a proximal handle portion 126 that either includes manifold 114 or is affixed to the rear of the manifold 114. The handle assembly 123 also includes the back handle portion 128, which may be releasably locked with the proximal handle portion 126, thereby preventing the back handle portion from rotating unintentionally.

Figure 4:
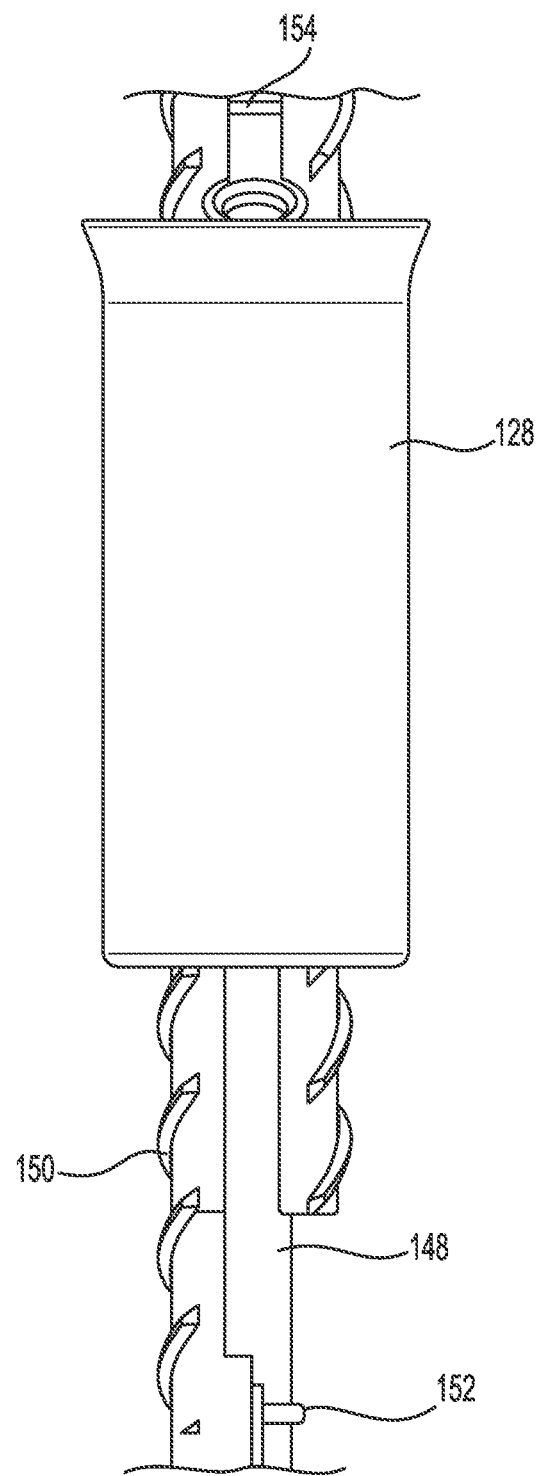
FIG. 4 is a partial cross-sectional view of a distal portion of the handle portion of the embodiment of the stent graft delivery device of FIG. 1.
Figure 5:
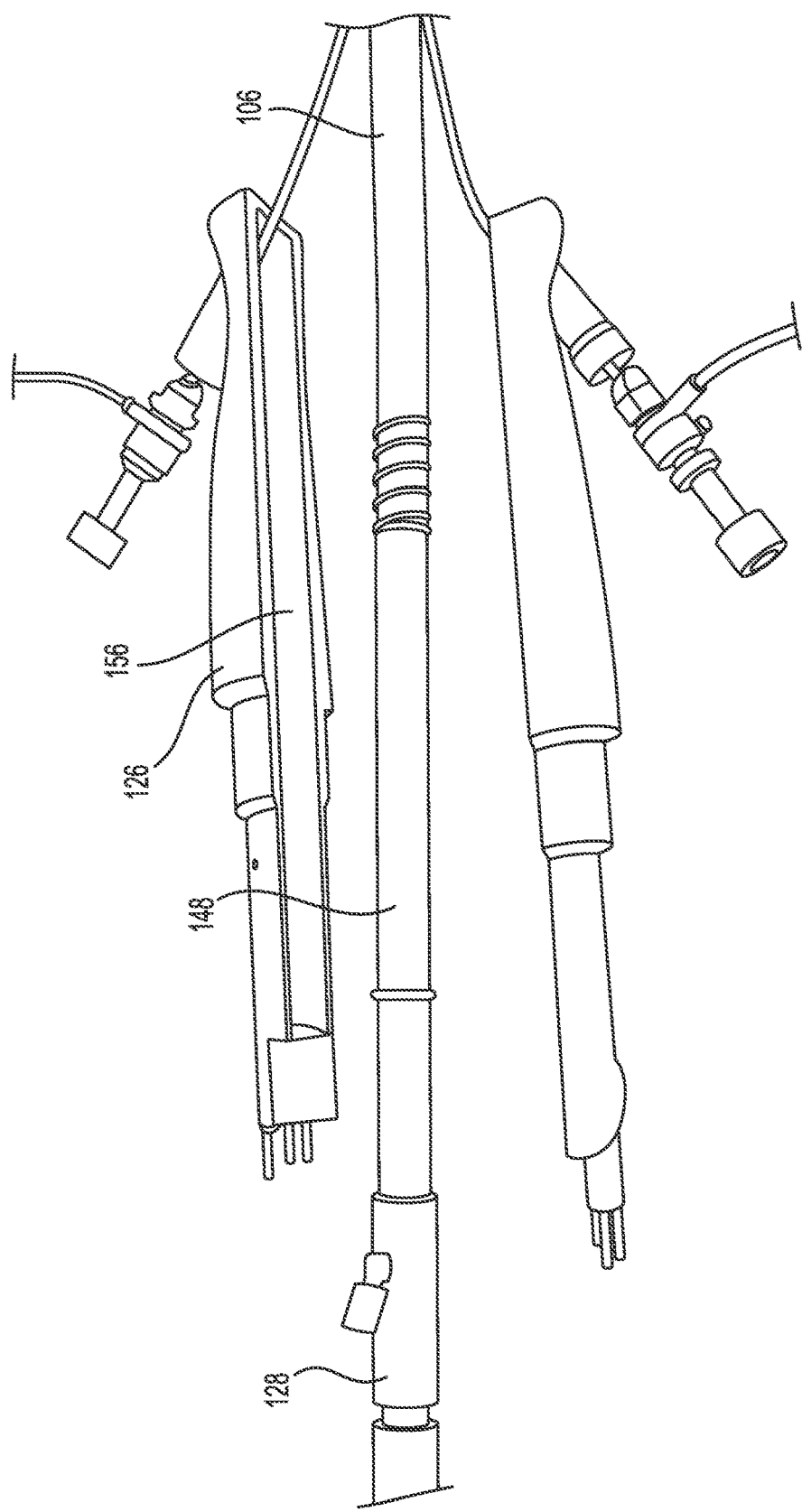
FIG. 5 shows the distal portion of the embodiment of the stent graft delivery device of FIG. 1 and in particular detail the handle portion.

As shown in FIGS. 3-5, the back handle portion 128 is disposed about a sheath mount 148. The sheath mount 148 extends through the handle assembly 123 as shown in FIG. 5. As shown in FIG. 5, the sheath mount 148 is received within an inner groove 156 formed within the front handle 126.

As better shown in FIGS. 4 and 5, the sheath mount 148 is in communication with three parts in the device 100. The first is the split flexor 106, which is fixed to the sheath mount 148 by a pin vice or an adhesive. As shown in FIG. 5, the distal end of the sheath mount 148 is coupled with to the proximal end 109 of the sheath 106. A compression spring 158 attaches the sheath 106 to the sheath mount 148. Other fastening mechanisms, such as a compression band or clip, may be used to attach these components together. The sheath mount 148 is also in communication with the tri lumen pusher (not shown). The sheath mount 148 slides over the top of the tri-lumen pusher (not shown) and is kept concentric to the rest of the device 100. The sheath mount 148 is also coupled with the back handle 128. A portion of the back handle 128 mates with the sheath mount 148 and pushes it linearly as the back handle 128 is twisted along a series of threads 150. Specifically, the sheath mount 148 further includes an abutment portion 168 that engages the back handle 128 such that the sheath mount 148, and sheath 106, translate along the longitudinal axis of the sheath mount 106 as the back handle 128 is rotated.

As shown in FIG. 4, the series of threads 150 is disposed along a portion of the length of the sheath mount 148. The back handle portion 128 is slidingly received over the series of threads 150 such that the back handle portion can rotate about the sheath mount 148 along the threads 150. The back handle portion 128 travels along a longitudinal axis defined by the length of the sheath mount 148 as it is rotated. The sheath mount 148 includes front and back O-rings 152, 154 to seal any space between the shaft mount 148 and threads 150. Distal to the back handle 128 is a trigger wire release mechanism 159.

In the embodiment shown in FIG. 1, trigger wire release mechanism 159 includes the trigger wire releases 160, 162, 164, 166 are releasably mounted to the sheath mount 148 and distal to the back handle 128. Trigger wire release 160 is for the release of the stabilization retention of indwelling guide wires. Trigger wire release 162 is for diameter reducing ties for the stent graft 131. Trigger wire release 164 is for a retention trigger wire for an exposed stent 137 of the stent graft 131 in the capsule. Trigger wire release 166 is for the distal end of the stent graft 131. It is appreciated that the number of trigger wire releases will vary depending on the number of stents to be deployed within the vessels. Other trigger wire release mechanisms are contemplated for use with the present invention.

Figure 6:
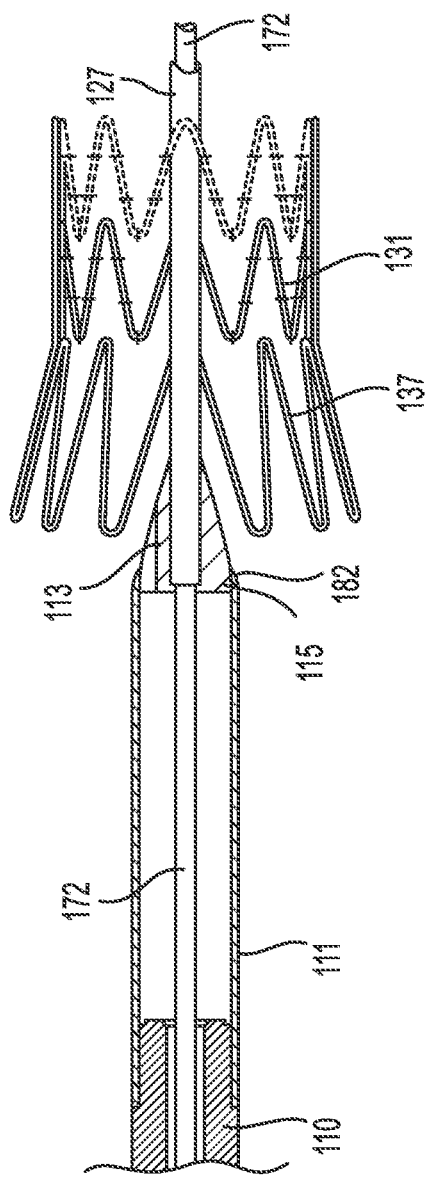
FIG. 6 shows a cross-sectional view of part of a nose cone dilator and capsule of the stent graft delivery device of FIG. 1.

As shown FIGS. 1 and 6, the introduction portion 104 of the stent graft delivery device 100 includes the nose cone dilator 110 and at the distal end of the nose cone dilator 110 is a distally opening capsule 111 for the receipt of an exposed stent 137 of a stent graft 131. The capsule 111 has a slightly in-turned distal end 182. This has two purposes, a first is to assist with engagement of the sheath 106 of the delivery device when the nose cone dilator 110 is retracted into the sheath 106 and a second is to prevent complete withdrawal of a distal retrieval taper device 113 from the capsule as will be discussed below. A guide wire catheter 172 passes through and is fastened to the nose cone dilator 110 at its proximal end and passes through the handle assembly 123 of the delivery device 100. A pin vice arrangement 170 at the distal end of the back handle portion 128 locks movement of the guide wire catheter 172 with respect to the distal portion of the handle 128 and can be loosened to allow relative motion between these components.

Figure 7:
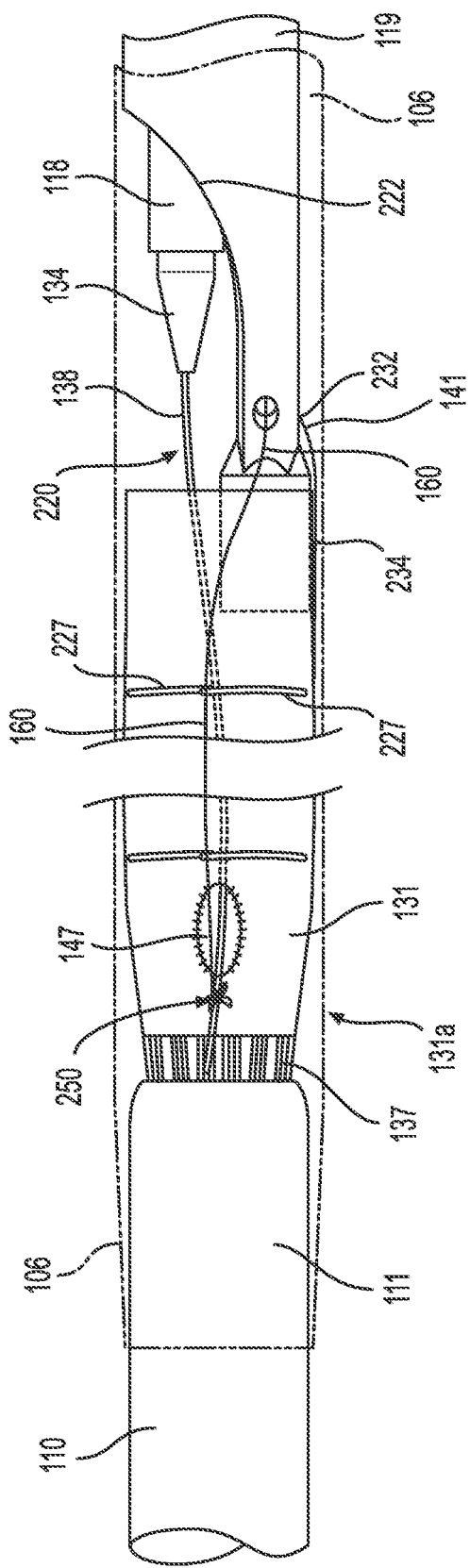
FIG. 7 shows a schematic detailed side view of a stent graft retained on the stent graft delivery device of FIG. 1.

The stent graft 131 shown in FIG. 6 comprises a tubular body of a biocompatible graft material such as Dacron, expanded PTFE or Thoralon, a polyurethane material. The stent graft is supported by self-expanding stents (not shown for clarity). The proximally extending exposed stent 137 assists with providing infra-renal fixation of the deployed stent graft. As shown in FIG. 7, the stent graft has two fenestrations 147 which are provided to give access to the renal arteries. The stent graft 137 is retained on the delivery device 100 by proximal retention of the exposed stent 137 into the capsule 111 of the delivery device and distally by a trigger wire release mechanism 159. Diameter reducing ties can be used to hold the stent graft in a diameter reduced condition during the initial catheterisation of a side branch because it may still be necessary to move the stent graft proximally or distally or rotate it. In the diameter reduced condition this is still possible whereas when released to full diameter this may not be possible.

U.S. patent application Ser. No. 11/507,115, filed Aug. 18, 2006 entitled "Assembly of Stent Grafts" teaches the use of diameter reducing ties for stent grafts and the teachings therein are incorporated herein in their entirety. U.S. Pat. No. 7,435,253 entitled "Prosthesis and a Method of Deploying a Prosthesis" teaches arrangements for retaining a stent graft or prosthesis on a delivery or deployment device and allowing for independent rotational and translational movement of each end of the stent graft and the teachings therein are incorporated herein in their entirety.

As can be seen in FIG. 6, the distal retrieval taper device 113 fits coaxially around the guide wire catheter 172 and can move longitudinally along the guide wire catheter 172. A retrieval catheter 127 is disposed coaxially around the guide wire catheter 172 and can move longitudinally along the guide wire catheter 172. At its proximal end, the retrieval catheter 127 may joined to the distal retrieval taper device 113 and at its distal end, the retrieval catheter 127 is joined to the front handle 126 by a suitable adhesive. The distal retrieval taper device 113 used with the embodiments of the present invention may include the retrieval taper device disclosed in U.S. Pat. No. 8,876,879, filed Jun. 4, 2009 and entitled "Introducer" teaches distal retrieval taper devices (referred to therein as tapered plugs) and the teaching therein is incorporated herein in its entirety.

The distal retrieval taper device 113 has an enlarged shoulder 115 at its proximal end. The shoulder is sized so that it is of greater diameter than the smallest part of the in-turned distal end 182 of the capsule 111. By this arrangement the distal retrieval taper device 113 can move through the capsule but cannot be fully removed from the capsule. The retrieval catheter 127 is coaxial with the guide wire catheter 172. At its proximal end, the retrieval catheter 127 is affixed to the distal retrieval taper device 113 and at its distal end the retrieval catheter 127 is affixed to the front handle portion 126. This means that movement of the guide wire catheter 172 proximally with respect to the distal handle portion 129 after the release of the pin vice 170 will move the nose cone dilator 110 and capsule 111 with respect to the distal retrieval taper device 113 with the effect that the distal retrieval taper device 113 extends from the capsule thereby providing a smooth tapered surface for retrieval of the nose cone dilator through the stent graft. Locking of the pin vice after the distal retrieval taper 113 has been moved to the distal end of the capsule 111 ensures that all of the distal retrieval taper device 113, the capsule 111, the nose cone dilator 110, and the distal handle portion 129 all move together.

By this arrangement, the nose cone dilator 110 can be moved to a distal position with respect to fenestrations 147 in the stent graft 131 so that the nose cone dilator 110 and distally opening capsule 111 neither interferes with the deployment of side branch covered or uncovered stent grafts through such fenestrations 147 nor does any subsequent retraction of the nose cone dilator 110 interfere with the deployed of side branch side branch covered or uncovered stent grafts. U.S. Pat. No. 8,118,854, filed Sep. 28, 2007 entitled "Endovascular Delivery Device" teaches apparatus and methods of deployment of stent grafts and side branch stent graft into fenestration of such stent grafts and the teaching therein is incorporated herein in its entirety. The use of the stabilization retention of the indwelling guide wire is particularly discussed therein.

Figure 8:
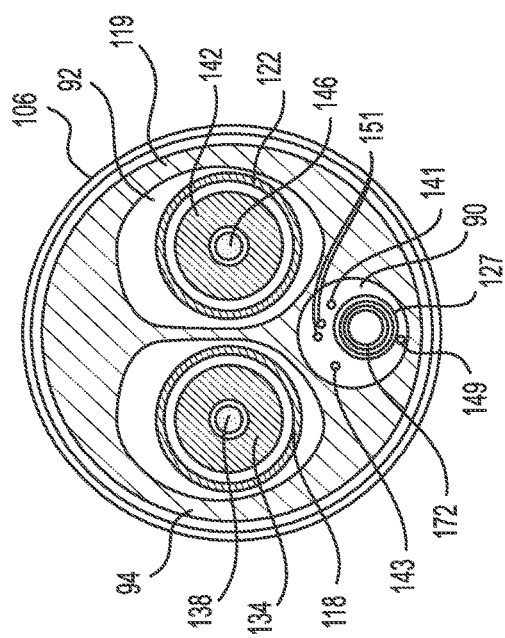
FIG. 8 shows a transverse cross-sectional view of the pusher catheter portion of the embodiment shown in FIG. 1.

As can be seen particularly in FIG. 8, which is a transverse cross section along the line 8-8' as shown in FIG. 1, the tri-lumen catheter 119 is surrounded by the sheath 106. In this embodiment, the tri-lumen catheter 119 has three longitudinally extending lumens. A first lumen is a guide wire lumen 90 and this lumen is off-set from the center of the tri-lumen catheter 119 to allow for two auxiliary lumens 92 and 94. The guide wire lumen 90 has passing through it the guide wire catheter 172 and coaxially around that the retrieval catheter 127.

Also in the guide wire lumen 90 are the trigger wires for the diameter reducing ties 149, the top capsule 143, the distal retention 141 and the auxiliary guide wire stabilization 151. The auxiliary lumen 94 has the first access sheath 118 extending through it and the dilator 134 and guide wire 138 extend through the first access sheath 118. The auxiliary lumen 92 has the second access sheath 122 extending through it and the dilator 142 and guide wire 146 extend through the second access sheath 122.

Figure 9:
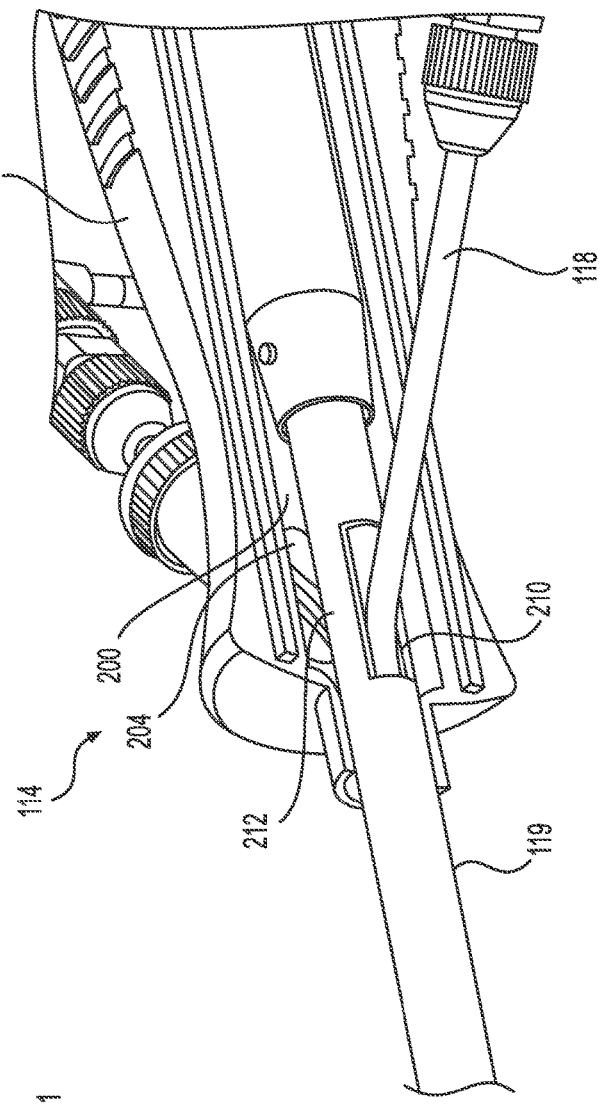
FIG. 9 shows a partial cross-sectional view of a handle portion of the embodiment of the stent graft delivery device of FIG. 1 with the auxiliary lumens extending therefrom.
Figure 10:
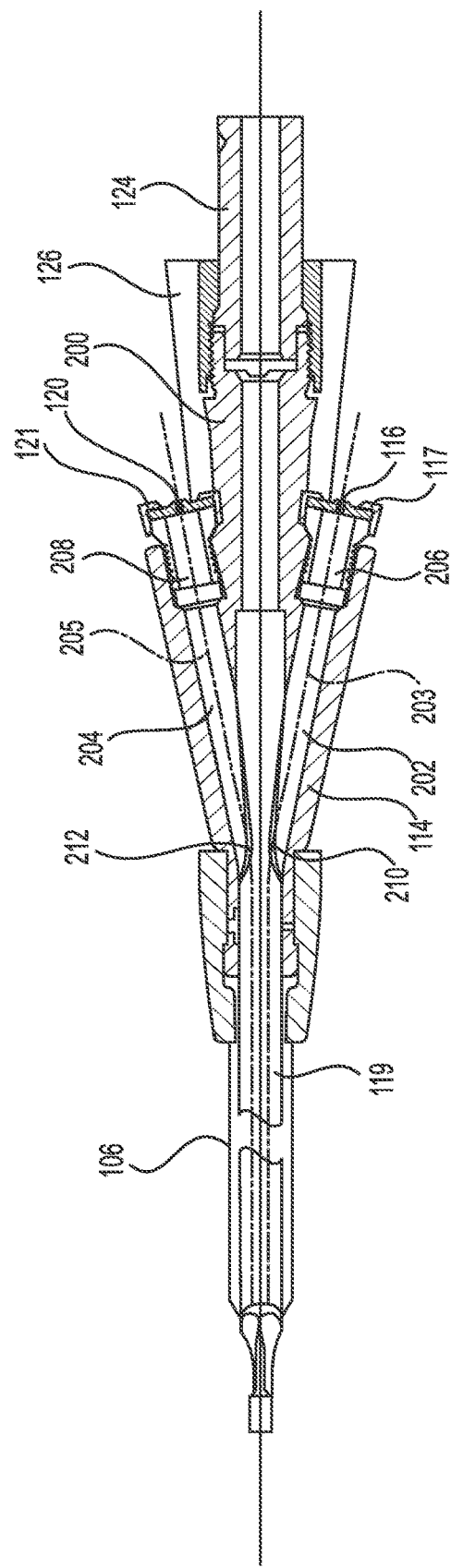
FIG. 10 shows a cross-sectional view of an assembly of a manifold and pusher chatter of the embodiment of the stent graft delivery device of FIG. 1.

The relationship between the manifold 114, the front handle 126, and the sheath 106 is shown in more detail in FIGS. 2, 3, 9, and 10. As shown in FIGS. 3, 9, and 10, the manifold 114 forms part of the front handle 126 in this embodiment and includes a through bore 200 and angled side ports 202 and 204. As can be seen in FIGS. 9, 10 and 11A to 11D, the tri-lumen catheter 119 has two side apertures or windows 210 and 212 which open from the side of the tri-lumen catheter 119 into the respective lumens 92 and 94. These side apertures are elongate and tapered towards the distal end. When the tri-lumen catheter 119 is pushed into the through bore 200 of the manifold 114, the side apertures in the tri-lumen catheter 119 align with the respective angled side ports 202 and 204 of the manifold 114 thereby providing an uninterrupted lumen from the access port 116 for the first access sheath 118 into the pusher lumen 94 along the dotted line 203 and from access port 120 for a second access sheath 122 into the pusher lumen 92 along the dotted line 205 as shown in FIG. 10.

Figure 11D:
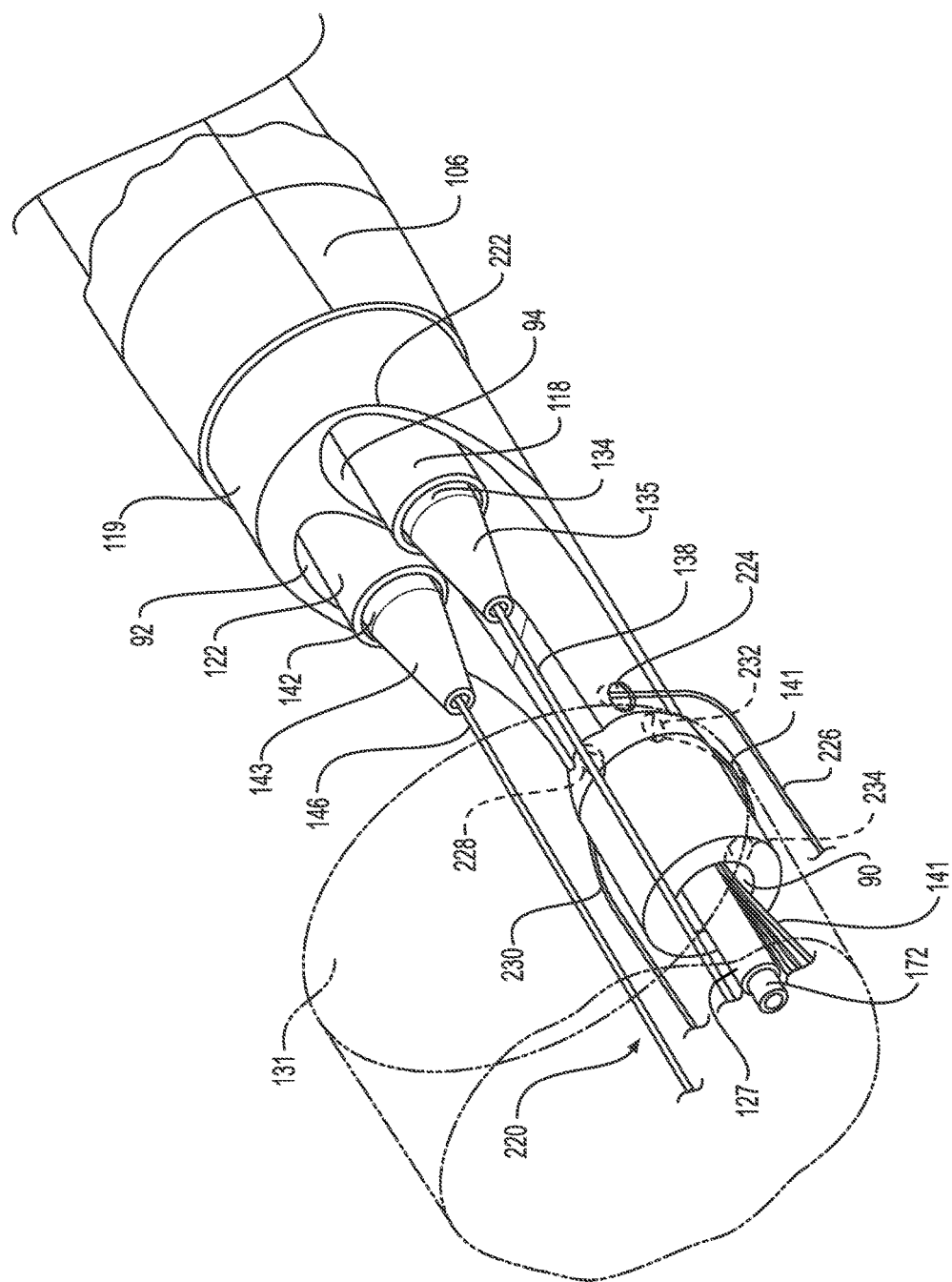

As can be best seen in FIG. 11A to 11D, at the proximal end of the tri-lumen catheter 119 is an attachment boss 220 and a scalloped end 222 to provide exit ports for the two auxiliary lumens 92 and 94. The guide wire lumen 90 opens out at the proximal end of the attachment boss 220 and to each side of the attachment boss there are apertures for trigger wires. As shown in FIG. 11D, aperture 224 is for trigger wire 226 which is used for the diameter reducing ties on one side of the stent graft 131. A corresponding aperture 228 and the other side of the attachment boss 220 is for the trigger wire 230 for the other side of the stent graft 131.

Trigger wire 141 extends out of aperture 232 in the attachment boss 220 and engages into the stent graft 131 before re-entering the attachment boss at aperture 234 and exiting the guide wire lumen 90 at the proximal end of the tri-lumen catheter 119.

In one embodiment of the present invention, the access sheaths (or access sheaths) 118, 122 terminate out of the renal fenestrations on top of the graft material. The access sheaths 118, 122 are preloaded through the graft fenestrations and are disposed within the manifold 114, which forms part of the front handle 126. Stent grafts for stenting side branches are preloaded in the access sheaths 118, 122 so as to allow for the cannulation of side branches after the main stent graft has been deployed at the desired location.

The sheath 106 is disposed between the tri-lumen catheter 119 and the bore 200. As better shown in FIG. 2, a portion of the sheath 106 includes a split 176 on either side so as to allow access into the interior of the sheath 106. The splits 176 are formed at least partially along the length of the sheath 106 so as to allow access sheaths 118, 122 to be disposed through the splits 176 and into the tri apertures 210, 212 of the tri-lumen catheter 119. The splits 176 allow for the preloading of the access sheaths 118, 122. The gap of the split 176 is sufficiently large enough to allow for the sheath 106 to be retracted while the access sheaths 118, 122 are preloaded within the manifold 114. Thus, the maximum opening of each split 176 may be equal to the outer diameter of the access sheaths 118, 122, which in one embodiment is 6 Fr. The length of each split 176 varies and can be as small as 1 mm or as long as 40 mm or greater. The length of the splits 176 may extend from a proximal end of the sheath 106 and may terminate at a location of the sheath 106 that is distal to the handle assembly 123.

The splits 176 allow the sheath 106 to be retracted, by rotation of the back handle 128, while the access sheaths 118, 122 remain in the tri lumen catheter 119. As shown in FIGS. 2 and 9, the splits 176 allow for continuous access to the tri-lumen catheter 119 via the apertures 210, 212 during deployment process of the main stent graft 131. This allows the main stent graft 131 to be deployed while the access sheaths 118, 122, which contain the pre-loaded stent grafts for the side branches, remain in the tri-lumen catheter 119. Upon deployment of the main stent graft 131, the side branch stent grafts may be inserted in the side branches in the matter described below so as to cannulate the side branches. The step of inserting the access sheaths 118, 122 into the manifold 114 after the deployment of the main stent graft 131 and the related steps are eliminated.

Further, the access sheaths 118, 122 (left and right) on their respective indwelling guide wires 138 146 will already be disposed within the lumen of stent graft 131 such that the step of advancing the access sheaths 118, 122 and guide wires 138, 146 within the lumen of the stent graft 131 after the placement of the device 100 within the patient is not required.

A secondary sheath 178, shown in FIGS. 2 and 3, is disposed about the sheath 106. The length of the secondary sheath 178 is approximately equal to the length of the splits 176 in the sheath 106. The function of the thin secondary sheath is to direct blood flow from the splits 176 in the sheath 106 back into the patient's body.

Extending out of the two auxiliary lumens 92 and 94 are the auxiliary catheters 122 and 118 respectively. From the proximal ends of the respective auxiliary catheters 118 and 122 extend dilators 134 and 142. The auxiliary guide wires 138 and 146 extend through the dilators and the secondary stents are also disposed therein.

FIG. 7 shows detail of the stent graft 131 and its retention system in the region 107 as shown in FIG. 1. In particular there is detail shown of the distal attachment, the diameter reducing ties and the proximal retention. The stent graft 131 is retained within the sheath 106 and concentrically around the guide wire catheter 172 and retrieval catheter 127. The stent graft 131 has a fenestration 147 towards its proximal end. In use, the stent graft 131 is deployed so that the fenestration 147 is substantially aligned with a renal artery and it is intended to catheterize the renal artery through the fenestration to deploy the secondary stent graft. The secondary stent graft can be covered or uncovered side branch stent or stent graft for cannulation of the renal artery.

The stent graft 131 has a proximally extending exposed stent 137 at is proximal end 131a. In as ready to deploy condition, the proximally extending exposed stent 137 is received into the capsule 111 at the distal end of the nose cone dilator 110. At its distal end 131b the stent graft is retained to the attachment boss 220 at the proximal end of the tri-lumen catheter 119. Trigger wire 141 engages the distal end of the stent graft. Trigger wire 141 extends out of aperture 232 in the attachment boss 220 and engages into the stent graft 131 before re-entering the attachment boss through aperture 234 into the guide wire lumen 90 and exiting the guide wire lumen 90 at the proximal end of the tri-lumen catheter 119. At its distal end the trigger wire 141 is attached to the trigger wire release 166.

The stent graft 131 has diameter reducing tie arrangements to retain it in a partially diameter reduced condition even after the sheath 106 has been retracted during deployment. The diameter reducing tie arrangement are on each side of the stent graft and comprise a trigger wire 160 stitched along the graft material on either side of the stent graft and loops of filament such as suture thread 227 engaged around the trigger wire and a portion of the graft material part way around the stent graft and then drawn tight. It can be appreciated that the secondary stent grafts may also be retained within the tri lumen catheter 119 in the same manner described above with respect to the stent grant 131. U.S. patent application Ser. No. 11/507,115, filed Aug. 18, 2006 entitled "Assembly of Stent Grafts" teaches apparatus and methods of diameter reduction of stent grafts and the teaching therein is incorporated herein in its entirety.

Figure 12:
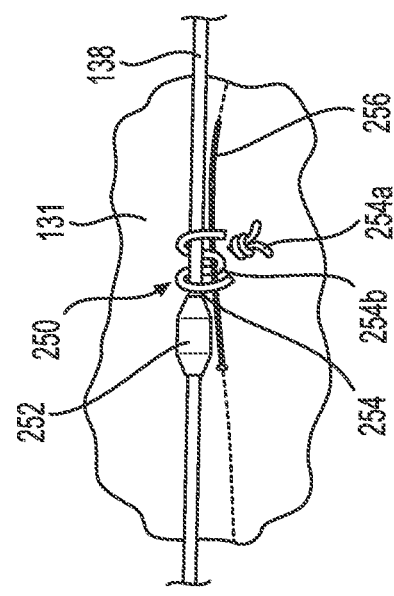
FIG. 12 shows a method of releasable retention of the indwelling guide wire of the embodiment of the stent graft delivery device shown in FIG. 1.

FIG. 12 shows detail of the retention system 250 by which the guide wires 138 (for instance) is stabilized proximally of the fenestration 147 (for instance). The guide wire 138 has a protrusion 252 which can be fastened with respect to the guide wire by solder, crimping, welding or gluing. A suture thread 254 is looped 254b around the guide wire 138 distally of the protrusion 252 and around a release wire 256 which is stitched through the material of the stent graft 131 and then the suture thread 254 is sewn at 254a into the material of the stent graft 131. When the release wire 256 is retracted the loop 254b of the suture thread 254 is released and the guide wire 138 can be retracted. In the meantime the retention system stabilizes the guide wire.

Figure 13:
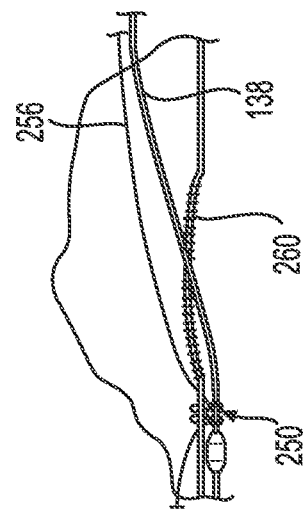
FIG. 13 shows an embodiment of fenestration suitable for the embodiment of the stent graft delivery device shown in FIG. 1.

FIG. 13 illustrates a cross section of a simple fenestration in cross section with the stabilized auxiliary guide wire extending through it. In this embodiment the fenestration 260 is reinforced with a ring of resilient wire such as nitinol wire. The auxiliary guide wire 138 passes through the fenestration and is restrained just proximal of the fenestration using a retention system 250 as shown in FIG. 13. U.S. Pat. No. 7,413,573, filed Oct. 12, 2004 entitled "Fenestrated Stent Grafts" teaches fenestrations in stent grafts and the teaching therein is incorporated herein in its entirety.

In the embodiment of the delivery device shown in FIGS. 1 to 13 the following components are present:

1. Guide wire catheter 172 extending from a handle 123 to a nose cone dilator 110.
2. Handle assembly 123 comprising a proximal handle portion 126 and a back handle portion 128.
3. Trigger wire release mechanism 159 that includes trigger wire releases 160, 162, 164, 166.
    a) Trigger wire release for top cap 164,
    b) Trigger wire release for diameter reducing ties 162
    c) Trigger wire release for stabilization retention of indwelling guide wire 160 on the distal portion of handle with respective trigger wires.
    d) Trigger wire release for distal end of the stent graft on back handle portion with respective trigger wire 141.
4. Tri-lumen catheter 119 with lumens for access sheaths 92, 94 and guide wire catheter 90 in communication with proximal handle portion 126 via manifold 114.
5. Sheath 106 with sheath hub 108 on tri-lumen catheter 119, the sheath 106 including splits 176.
6. Nose cone dilator 110 with a distally opening top capsule 111.
7. Indwelling guide wires 138, 146 through fenestrations 147 in stent graft 131 and into top capsule 111. Indwelling guide wires go through access sheaths 118, 122.
8. Stabilization retention system 250 of indwelling guide wires 138 and 146 proximally of fenestration 147.
9. Distal retrieval taper 113 in top capsule 111 coaxial with guide wire catheter 172 and a retrieval catheter 127 extending from retrieval taper 113 to and fixed to distal portion of handle 128.
10. Access sheaths 118 and 122 having dilators 134 and 142 respectively within them, where the access sheaths 118 and 122 are preloaded within the device;
11. Stent graft 131 with:
    a) Proximally extending exposed stent 137 received in top capsule 111 and a top cap trigger wire 143 retention;
    b) Distal retention;
    c) Fenestrations for renal arteries, for instance 147;
    d) Radiopaque markers (not shown); and
    e) Diameter reducing ties 227 and trigger wire 160.
12. Access sheaths 118, 122 disposed within auxiliary lumens 92, 94
13. Indwelling wire guides 138, 146 disposed within access sheaths 118, 122.
14. Buddy wire guides disposed within the access sheaths alongside the indwelling wire guides 138, 146.

Exemplary introduction steps may be as follows:

1. Position the introduction part 104 of the delivery device 100 into the aorta correctly taking into account N-S position as well as rotational position with respect to target vessels and fenestrations 147 on the stent graft 131 using markers on stent graft body. At this stage the delivery device is as shown in FIGS. 1 and 2.
2. Withdraw the outer sheath 106 of the delivery device while continuing to check position until the distal end of the stent graft 131 opens. The splits 176 of the sheath 106 widen so as to allow the sheath 106 to be retracted relative to the first and second access sheaths 118, 122 without disturbing the location of the first and second access sheaths 118, 122. At this stage the distal end of the stent graft 131 is still retained by distal fixation, the proximal end is retained by the exposed stent retained in top capsule 111 of the delivery device 100 and the expansion of the stent graft 131 is restricted by the diameter reducing ties 227.
3. Position the access sheaths 118, 122 (left and right) on their respective indwelling guide wires 138, 146 at the desired location within the lumen of stent graft 131 to or through the fenestration 147 (at this stage the top capsule 111 still retains the exposed stent 137 and the indwelling guide wires).
4. Position the first access sheath 118 at the opening of the fenestration 147.
5. Remove the dilator 134 of the first access sheath 118.
6. Advance buddy wire guide (4-5 Fr) disposed in the first access sheath into the target vessel (e.g. renal artery). The additional catheter may have a crooked, curled, hockey stick tip to facilitate access.
7. Release the stabilization retention system 250 of indwelling guide wires 138 via the trigger wire release 160.
8. Remove the additional catheter and replace the access sheath dilator 134 and dilator catheter over the stiffer wire in the target vessel and advance the access sheath 118, 122 over the stiffer wire into the target vessel. Withdraw the access sheath dilator.
9. Repeat steps 4 to 9 for the other of the target vessels.
10. Release the top capsule 111 by removing the locking trigger wire 143 via trigger wire release 164, releasing the pin vice 170 and advancing the top capsule 111 on the guide wire catheter 100 and release the top exposed stent 137. At the same time, the distally facing capsule moves proximally over the distal retrieval taper device 113 to allow the distal retrieval taper device 113 to extend from the distal end of the capsule 111.
11. Tighten the pin vice 170.
12. Retract the nose cone dilator 110, top capsule 111 and distal retrieval taper 113 past the fenestration 147 by removing the locking screw 125 and retracting the sheath 106 by rotating the back handle 128. This also releases the distal attachment via trigger wire 141 connected to trigger wire release 166.

13. One at a time, withdraw the access sheaths 118, 122 from the target vessels and deploy covered stents between the fenestrations 147 and target vessels and balloon expand if necessary including flaring within the main stent graft 131.

14. Remove both access sheaths 118, 122 and also the guide wires from the target vessels and withdraw them from the system 100.

15. Retract the nose cone dilator 110, top capsule 111 and distal retrieval taper 113 to the sheath 106.

16. Withdraw the entire assembly 100. Further deployment may include a bifurcated distal component.

Exemplary aspects of certain background steps are also disclosed in U.S. Pat. No. 8,709,061, filed Jun. 6, 2011, entitled "Pre-loaded Multiport Delivery Device," the entirety of which is incorporated herein by reference in its entirety.

Figure 14:
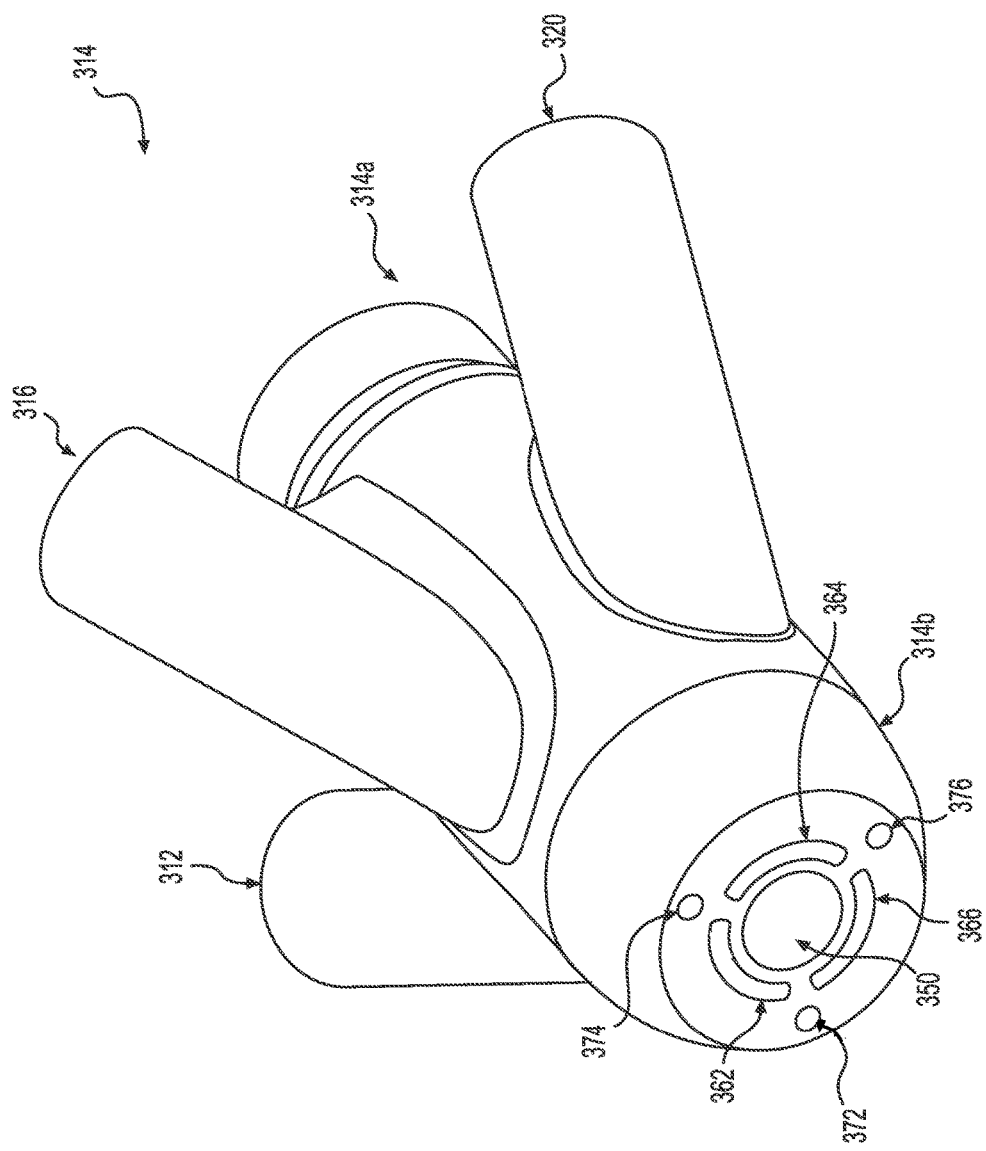
FIG. 14 shows an embodiment of a manifold suitable for the embodiment of the stent graft delivery device shown in FIG. 1.
Figure 15:
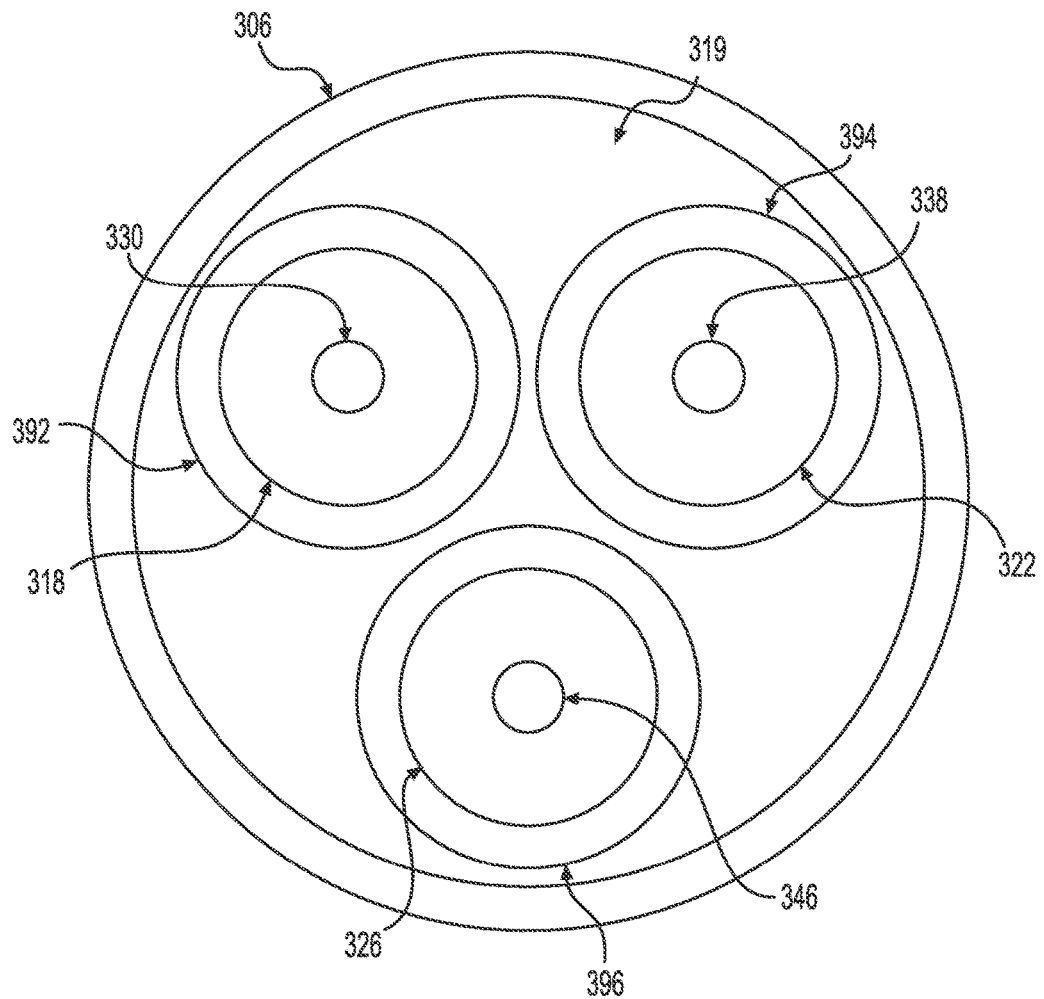
FIG. 15 shows a transverse cross-sectional view of an embodiment of a tri-lumen catheter suitable for the embodiment of the stent graft delivery device shown in FIG. 1.

FIG. 14 shows another embodiment of a manifold suitable for the embodiment of the stent graft delivery device shown in FIG. 1. A tri-lumen catheter 319, as shown in FIG. 15, extends from and is connected into a manifold 314 as is discussed in more detail below. The manifold 314 has a proximal end 314b into which is affixed the tri-lumen catheter 319 and three access ports 312, 316, 320 at its distal end 314a. The manifold 314 includes an access port 312 for a first access sheath 318, shown in FIG. 15, that extends from the manifold 314. Access port 316 is provided for a second access sheath 322, shown in FIG. 15. Access port 320 is provided for a third access sheath 326, shown in FIG. 15. The access ports 312, 316, 320 include haemostatic seals, which in one embodiment is 7 Fr.

As can be seen particularly in FIG. 15, which is a transverse cross-sectional view of an embodiment of a tri-lumen catheter suitable for the embodiment of the stent graft delivery device shown in FIG. 1, the tri-lumen catheter 319 is surrounded by a sheath 306. In this embodiment, the tri-lumen catheter 319 has three longitudinally extending auxiliary lumens 392, 394, 396. The auxiliary lumen 392 has the first access sheath 318 extending through it, and a guide wire 330 extends through the first access sheath 318. The auxiliary lumen 394 has the second access sheath 322 extending through it, and a guide wire 338 extends through the second access sheath 322. The auxiliary lumen 396 has the third access sheath 326 extending through it, and a guide wire 346 extends through the third access sheath 326. Advantageously, in this embodiment, separate dilators may not be needed within the three access sheaths 318, 322, 326, as this construction may provide a sufficient replacement for dilators. This can reduce the length of a handle of the stent graft delivery device by 35 cm.

Figure 16:
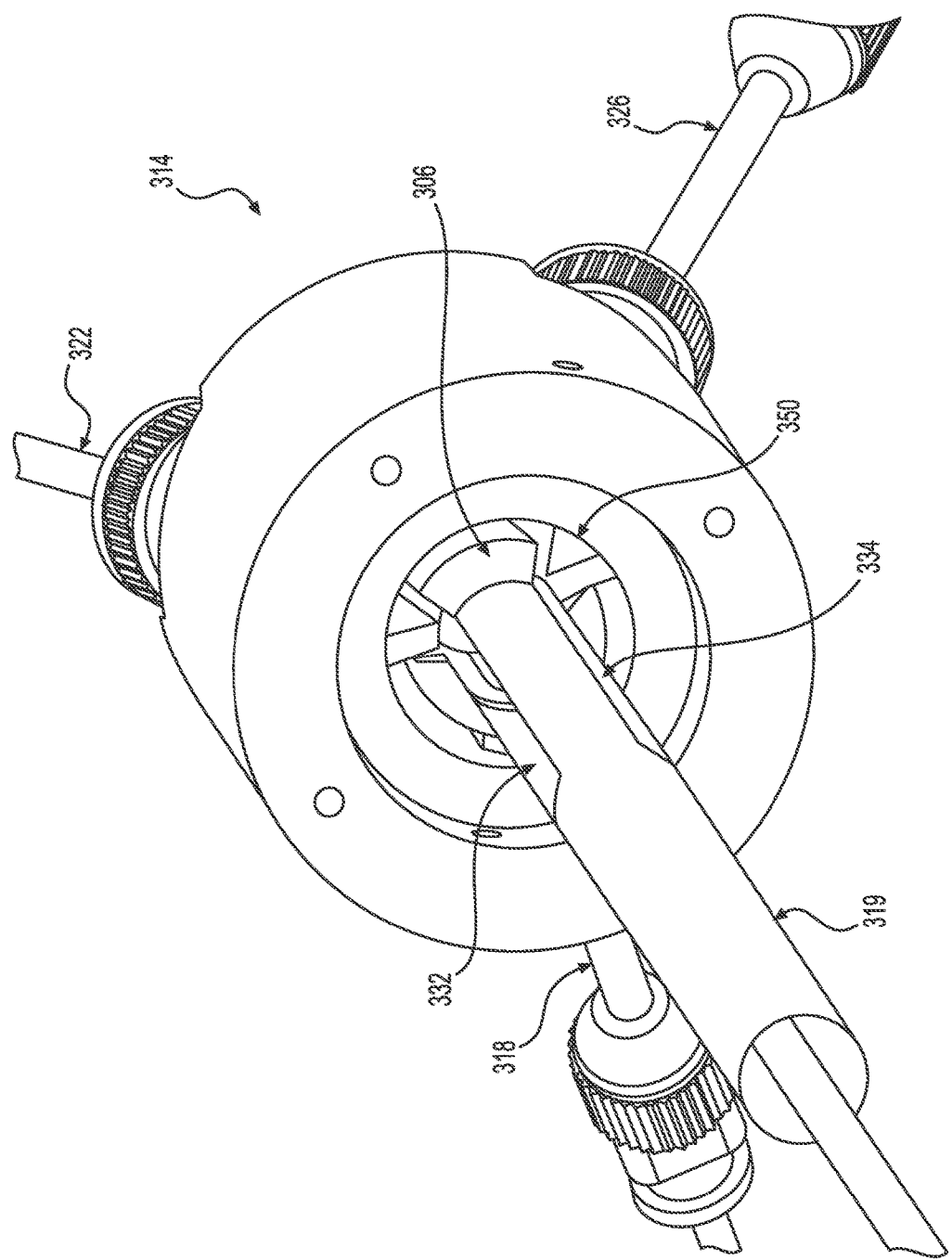
FIG. 16 shows a partial cross-sectional view of a manifold and a tri-lumen catheter suitable for the embodiment of the stent graft delivery device shown in FIG. 1.
Figure 17:
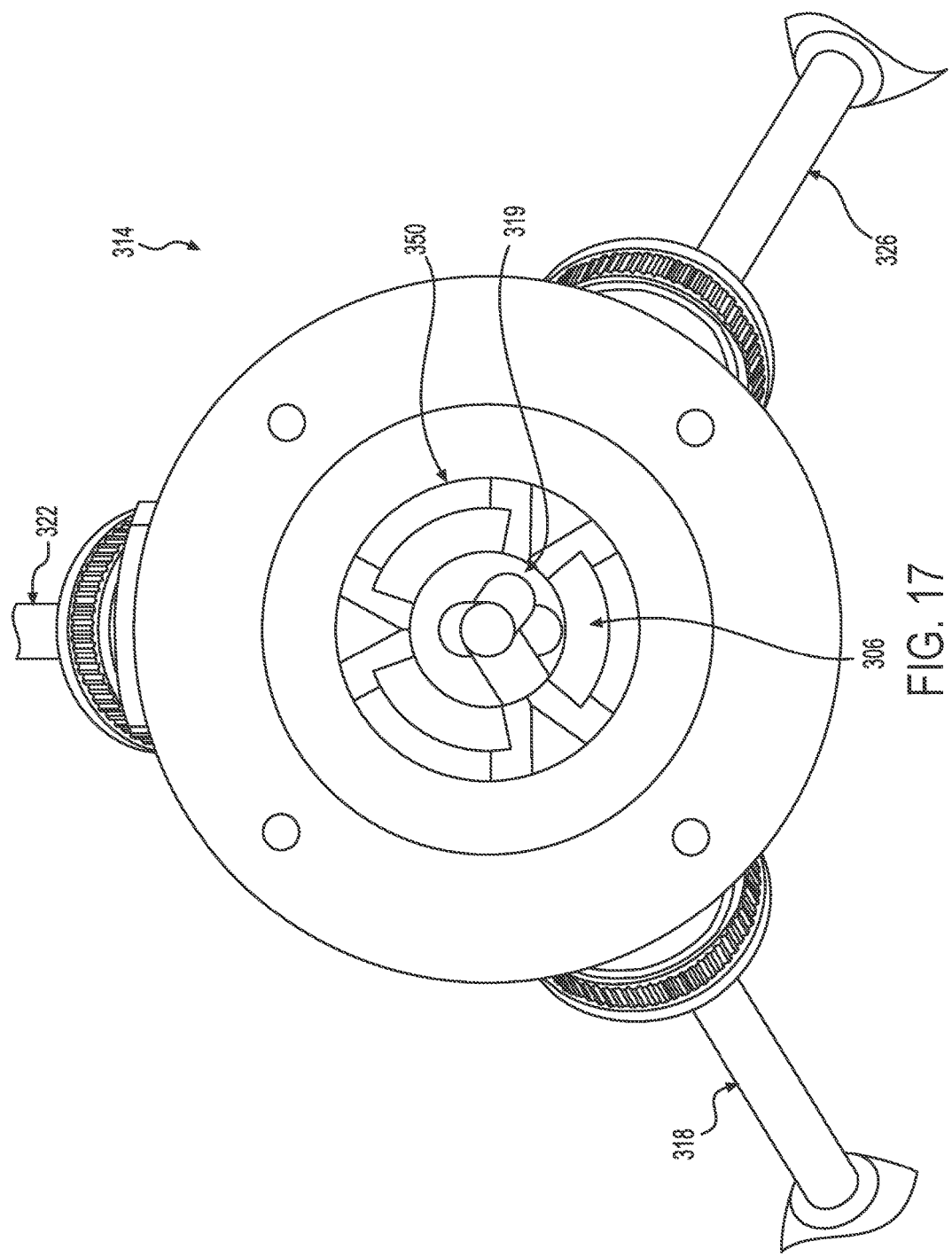
FIG. 17 shows a cross-sectional view of a manifold and a tri-lumen catheter suitable for the embodiment of the stent graft delivery device shown in FIG. 1.
Figure 18:
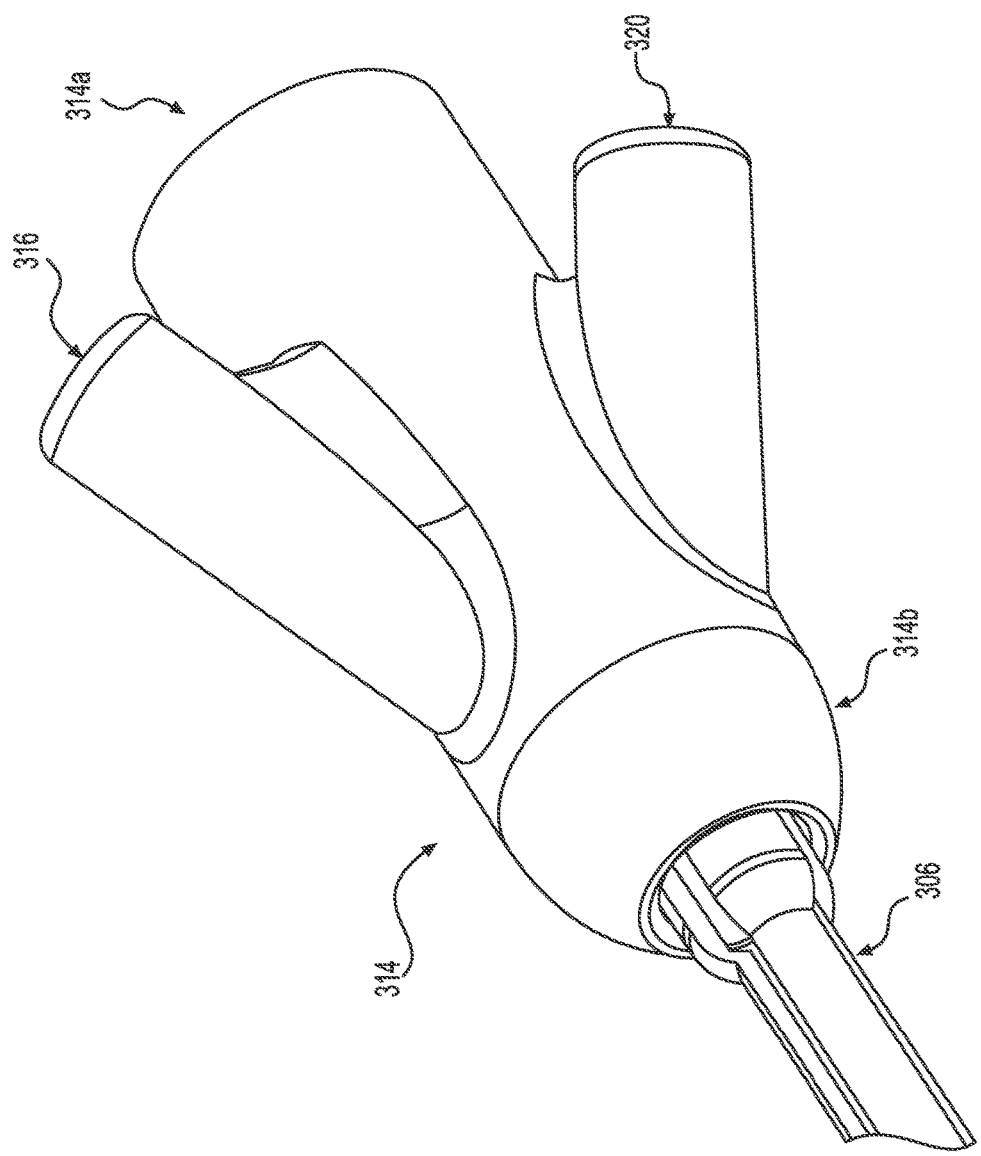
FIG. 18 shows an embodiment of a manifold and a tri-lumen catheter suitable for the embodiment of the stent graft delivery device shown in FIG. 1.
Figure 19:
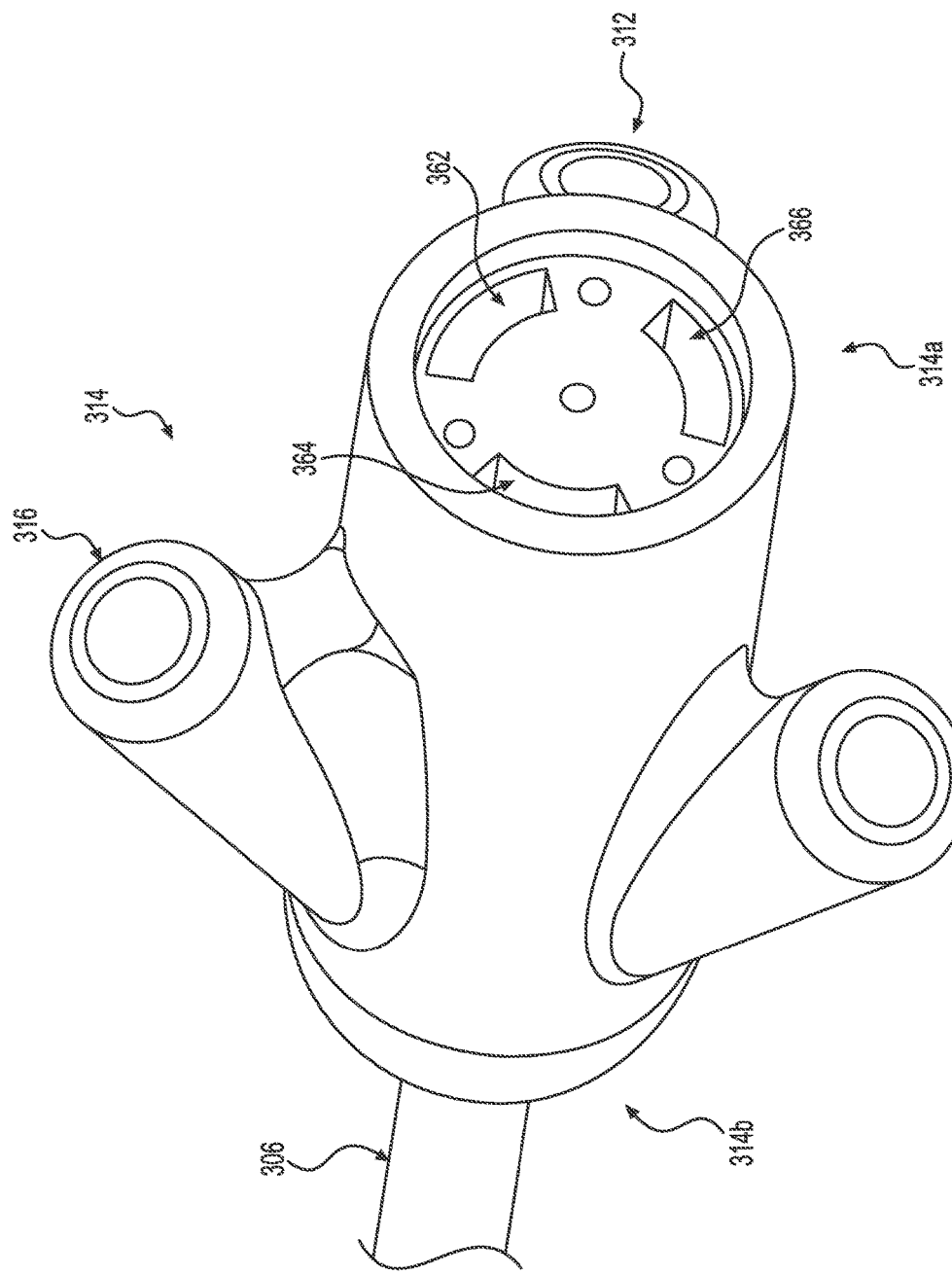
FIG. 19 shows a rear perspective view of a manifold suitable for the embodiment of the stent graft delivery device shown in FIG. 1.
Figure 20:
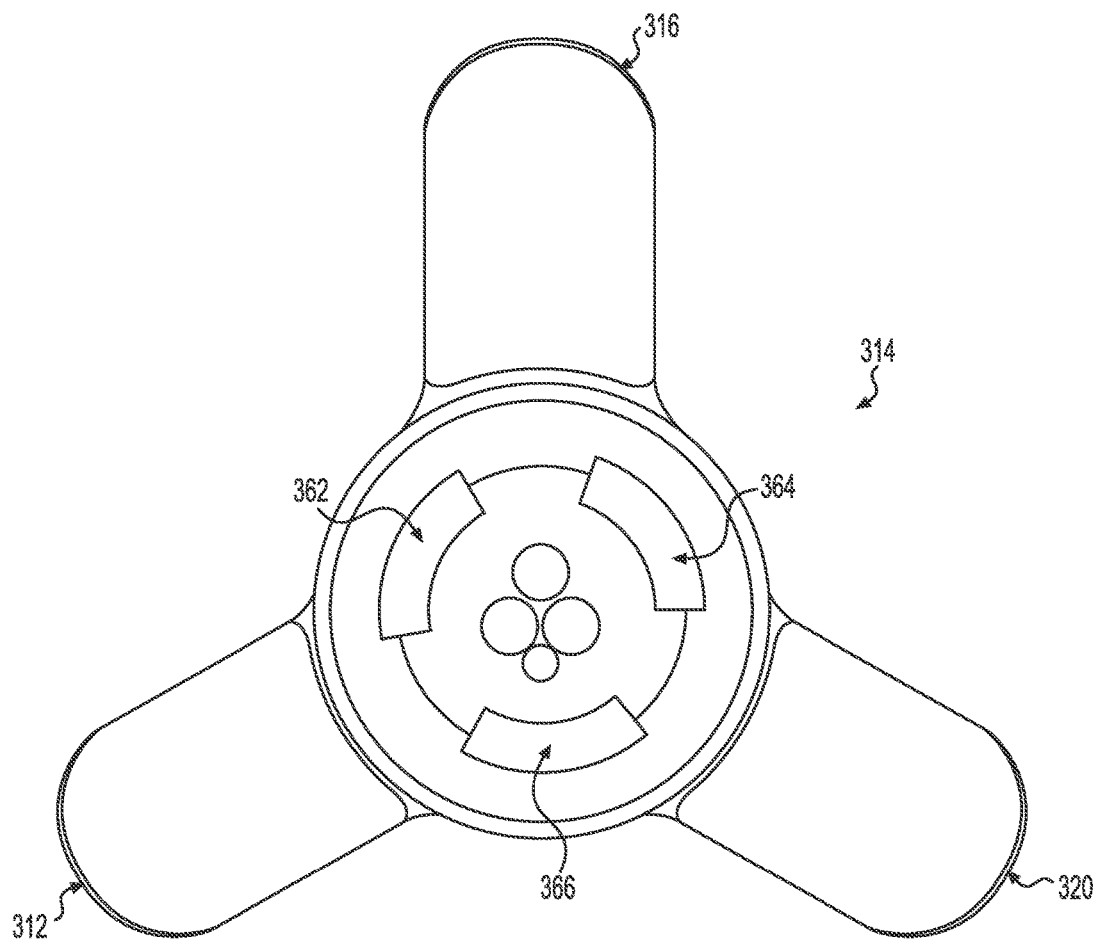
FIG. 20 shows a front perspective view of a manifold suitable for the embodiment of the stent graft delivery device shown in FIG. 1.
Figure 21:
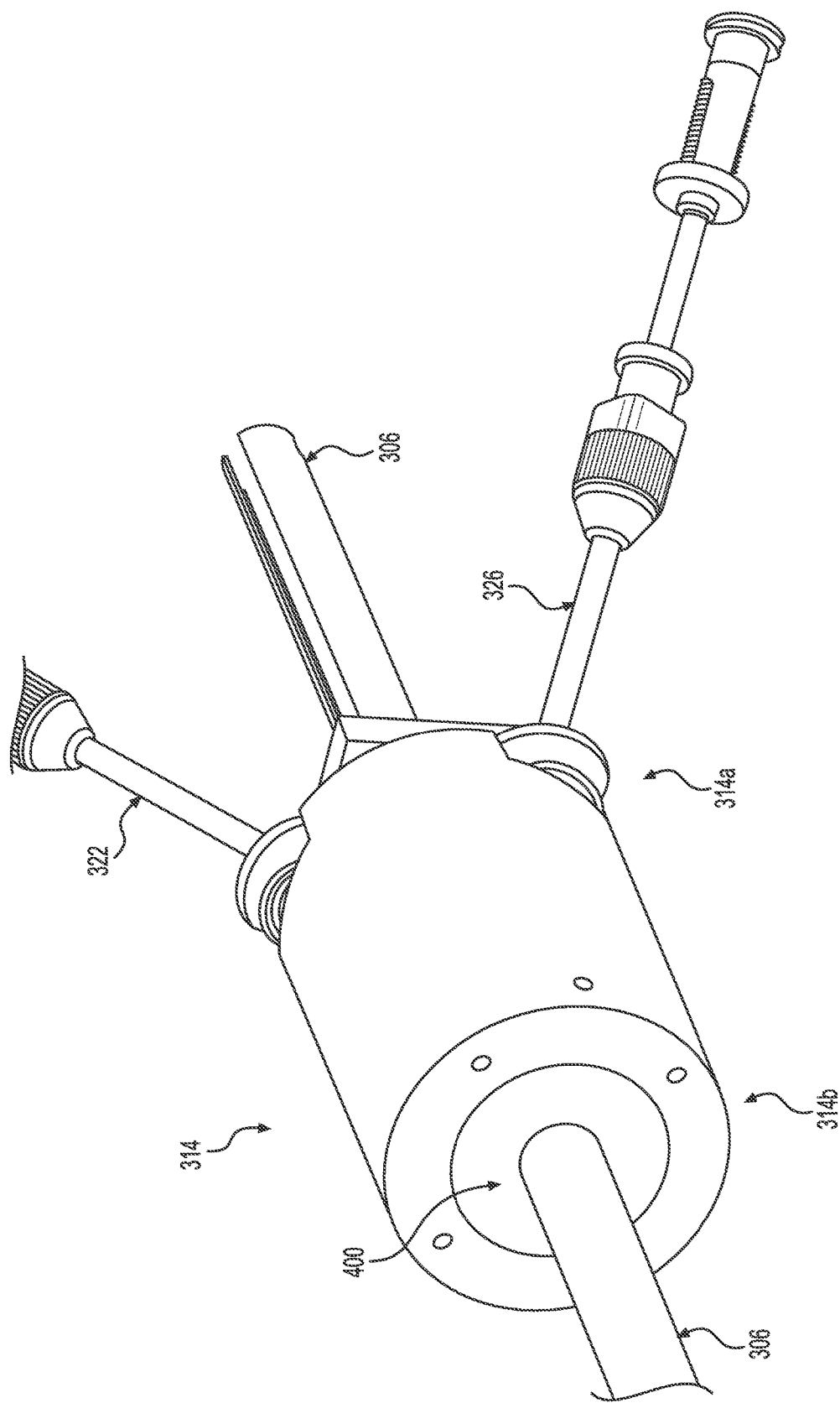
FIG. 21 shows an embodiment of a manifold and a cutter suitable for the embodiment of the stent graft delivery device shown in FIG. 1.

As shown in FIG. 16, the tri-lumen catheter 319 has three side apertures or windows 332, 334, 336 which open from the side of the tri-lumen catheter 319 into the respective auxiliary lumens 392, 394, 396. These side apertures 332, 334, 336 are elongate and tapered towards the distal end. When the tri-lumen catheter 319 is pushed into a central aperture 350 of the manifold 314, the side apertures 332, 334, 336 in the tri-lumen catheter 319 align with the respective access ports 312, 316, 320 of the manifold 314 thereby providing an uninterrupted lumen from the access port 312 for the first access sheath 318 into the auxiliary lumen 392, from access port 316 for a second access sheath 322 into the auxiliary lumen 394, and from access port 320 for a third access sheath 326 into the auxiliary lumen 396.

The access sheaths 318, 322, 326 terminate out of fenestrations along a graft material. The access sheaths 318, 322, 326 each have proximal regions that are preloaded through the fenestrations and each have distal regions that are disposed within the manifold 314. Stent grafts for stenting branch vessels may be preloaded in the access sheaths 318, 322, 326 so as to allow for the cannulation of branch vessels after the main stent graft has been deployed at the desired location. To fixate a distal end of the stent grafts, the guide wires 330, 338, 346 may have a thin, plastic tube affixed to them. The thin, plastic tube may comprise apertures for a distal trigger wire to fixate the distal portion of the stent graft.

As shown in FIGS. 17-21, the sheath 306 is disposed between the tri-lumen catheter 319 and the central aperture 350. A portion of the sheath 306 includes three splits to allow access into the interior of the sheath 306. The splits are formed at least partially along the length of the sheath 306 so as to allow access sheaths 318, 322, 326 to be disposed through the splits and into the side apertures 332, 334, 336 of the tri-lumen catheter 319. The splits allow for the preloading of the access sheaths 318, 322, 326. The gap of the splits is sufficiently large enough to allow for the sheath 306 to be retracted while the access sheaths 318, 322, 326 are preloaded within the manifold 314. The portions of the sheath 306 between the splits pass through three sheath apertures 362, 364, 366 when sheath 306 is retracted. The maximum opening of each split may be equal to the outer diameter of the access sheaths 318, 322, 326, which in one embodiment is 18 Fr. The length of each split varies and can be as small as 1 mm or as long as 15 mm or greater. To assist in opening the splits, a cutter 400 may be affixed to the proximal end 314b of the manifold 314 via three mounting holes 372, 374, 376.

Figure 22B:
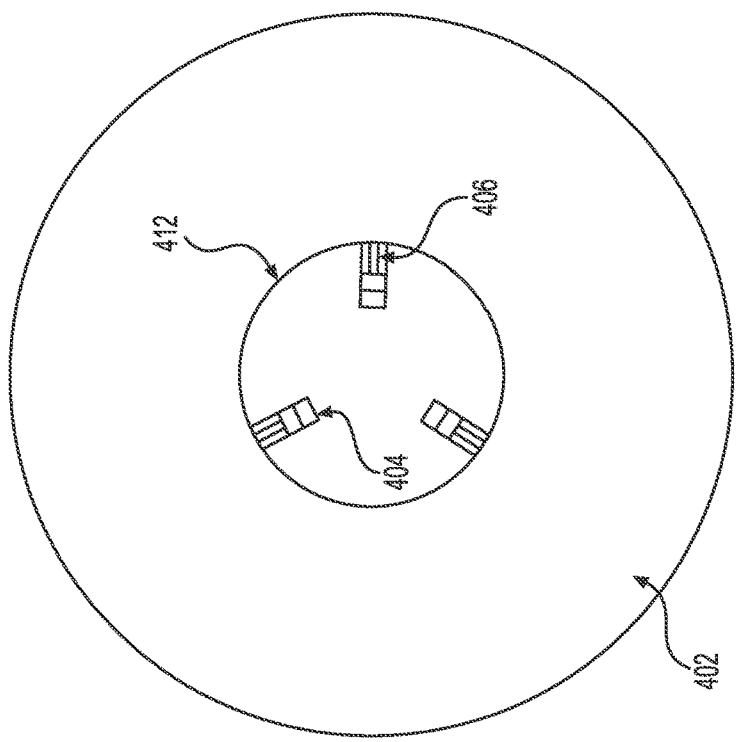
FIGS. 22A and 22B show front perspective views of a cutter suitable for the embodiment of the stent graft delivery device shown in FIG. 1.
Figure 22A:
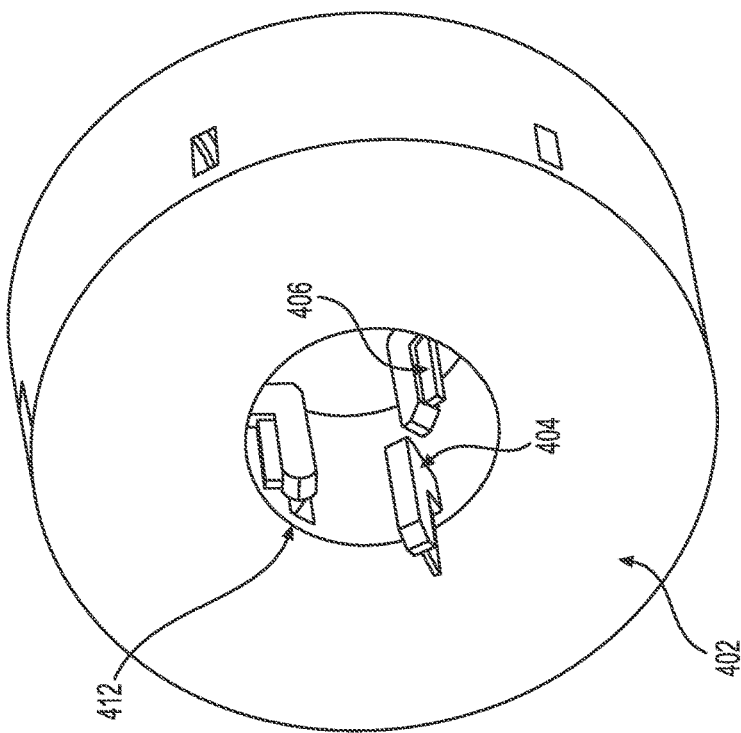

As shown in FIGS. 22A and 22B, the cutter 400 may comprise a fixture 402, at least one blade housing 404, and at least one blade 406. The fixture 402 may have an annular shape and comprise an aperture 412. The radius of the aperture 412 may be determined by the radius of the sheath 306. The at least one blade housing 404 may be attached to the aperture 412 of the fixture 402, and the at least one blade 406 may be attached to the at least one blade housing 404 with a sharp edge of the at least one blade 406 facing away from the at least one blade housing 404. The at least one blade housing 404 may hold the at least one blade 406 in place, prevent elements other than the sheath 306 from being pulled against the at least one blade 406, force the sheath 306 to be pulled into the at least one blade 406, and provide support for the at least one blade 406. The shape of the at least one blade housing 404 may resemble an "L," with one end of the "L" shape connecting to the aperture 412 and the at least one blade 406 connecting to the indented part of the "L" shape. Alternatively, the shape of the at least one blade housing 404 may resemble a "J."

The function of the cutter 400 may be shown in FIGS. 23A-23C. In FIG. 23A, the sheath 306 approaches a proximal end 410 of the cutter 400. The sheath 306 may or may not be pre-split. As shown in FIG. 23B, the sheath 306 passed through the cutter 400 so that the at least one blade 406 cuts the sheath 306. The cut sheath 306 can be seen exiting a distal end 411 of the cutter 400 in FIG. 23C. The number of blades 406 may determine the number of splits in the sheath 306.

Advantageously, by cutting the sheath 306 during the deployment process, the need for a pre-split sheath with an accompanying secondary sheath is eliminated, thus reducing the French size, providing greater control (for example, improved push control and/or torque control) of the system, and sealing the system.

Advantageously for the embodiment shown in FIGS. 14-15, a tri-lumen pusher may not be needed. Also, the superior mesenteric artery ("SMA") may be more easily cannulated and operation time may be decreased.

Additionally, instead of having a manifold with three access ports, it is understood that a manifold could have at least four ports to handle at least four access sheaths.

For the embodiment shown in FIGS. 14-15, exemplary introduction steps may be as follows:

1. Position the introduction part of the delivery device into the aorta correctly taking into account N-S position as well as rotational position with respect to target vessels and fenestrations on the stent graft using markers on stent graft body.

2. Withdraw the sheath 306 of the delivery device while continuing to check position until the distal end of the stent graft opens. The splits of the sheath 306 widen so as to allow the sheath 306 to be retracted relative to the access sheaths 318, 322, 326 without disturbing the location of the access sheaths 318, 322, 326. At this stage the distal end of the stent graft is still retained by distal fixation, the proximal end is retained by an exposed stent retained in a top capsule of the delivery device and the expansion of the stent graft is restricted by diameter reducing ties.

3. Position the access sheaths 318, 322, 326 on theft respective guide wires 330, 338, 346 at the desired location within the lumen of stent graft to or through the respective fenestrations (at this stage the top capsule still retains the exposed stent and the guide wires 330, 338, 346).

4. Position the first access sheath 318 at the opening of the fenestration.

5. Advance buddy wire guide (4-5 Fr) disposed in the first access sheath into the target vessel (e.g. renal artery). The additional catheter may have a crooked, curled, hockey stick tip to facilitate access.

6. Release a stabilization retention system of guide wire 330 via a trigger wire release.

7. Repeat steps 4 to 7 for the other of the target vessels (renal arteries and SMA).

8. Release the top capsule by removing a locking trigger wire via a trigger wire release, releasing a pin vice and advancing the top capsule on a guide wire catheter and release a top exposed stent. At the same time, the distally facing capsule moves proximally over a distal retrieval taper device to allow the distal retrieval taper device to extend from the distal end of the capsule.

9. Tighten the pin vice.

10. Retract the top capsule and distal retrieval taper past the fenestration by removing a locking screw and retracting the sheath 306 by rotating a back handle. This also releases a distal attachment via a trigger wire connected to a trigger wire release.

11. One at a time, withdraw the access sheaths 318, 322, 326 from the target vessels and deploy covered stents between the fenestrations and target vessels and balloon expand if necessary including flaring within a main stent graft.

12. Remove the access sheaths 318, 322, 326 and also the guide wires 330, 338, 346 from the target vessels and withdraw them from the system.

13. Retract the top capsule 111 and distal retrieval taper 113 to the sheath 306.

14. Withdraw the entire assembly. Further deployment may include a bifurcated distal component.

Exemplary aspects of certain background introduction steps are also disclosed in U.S. Pat. No. 8,709,061, filed Jun. 6, 2011, entitled "Pre-loaded Multiport Delivery Device," the entirety of which is incorporated herein by reference in its entirety.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

The invention claimed is:

1. A pre-loaded stent graft delivery device comprising:
a guide wire catheter having a guide wire lumen therethrough;
a handle assembly at a distal end of the guide wire catheter, the handle assembly including a manifold, where the manifold comprises two side ports and a through bore, the two side ports extending distally from the through bore;
a nose cone dilator at the proximal end of the guide wire catheter;
a pusher catheter extending from the manifold towards the nose cone dilator, the pusher catheter comprising at least one lumen therethrough where the guide wire catheter extends through the at least one lumen within the pusher catheter;
an access sheath disposed within each of the two side ports of the manifold; and
a sheath disposed coaxially over the pusher catheter, where the sheath has at least two longitudinal splits formed along the length of the sheath from the distal end of the sheath to the manifold, where each split is aligned with each of the access sheaths such that the sheath can be at least partially retracted over the access sheaths.

2. The pre-loaded stent graft delivery device of claim 1 further comprising a rotatable handle that forms part of the handle assembly.

3. The pre-loaded stent graft delivery device of claim 2 where the handle is rotatably coupled with the sheath so that the rotation of the handle in one direction retracts the sheath.

4. The pre-loaded stent graft delivery device of claim 1 wherein the pusher catheter further comprises two longitudinal auxiliary lumens.

5. The pre-loaded stent graft delivery device of claim 4 wherein the pusher catheter further comprises a proximal end spaced distally from the nose cone dilator and thereby defining between the proximal end of the pusher catheter and the nose cone dilator a stent graft retention region.

6. The pre-loaded stent graft delivery device of claim 5 further comprising a stent graft being releasably retained on the stent graft retention region.

7. The pre-loaded stent graft delivery device of claim 6 further comprising an indwelling guide wire within each access sheath.

8. The pre-loaded stent graft delivery device of claim 7 wherein each indwelling guide wire extends proximally of the access sheath through the stent graft and exits a respective fenestration in a wall of the stent graft.

9. The pre-loaded stent graft delivery device of claim 8 further comprising a dilator extending through each access sheath and comprising a dilator tip at a proximal end of the access sheath, the dilator being able to be withdrawn through the access sheath.

10. The pre-loaded stent graft delivery device of claim 9 wherein each side port has a haemostatic seal assembly and the respective access sheaths extend through the respective haemostatic seal assembly.

11. A pre-loaded stent graft delivery device comprising:
a guide wire catheter having a guide wire lumen therethrough;
a handle assembly at a distal end of the guide wire catheter, the handle assembly including a manifold, where the manifold comprises two side ports and a through bore, the two side ports extending distally from the through bore;
a handle forming part of the handle assembly, the handle rotatable about the guide wire catheter,
a nose cone dilator at the proximal end of the guide wire catheter;
a pusher catheter extending from the manifold towards the nose cone dilator, the pusher catheter comprising at least one lumen therethrough where the guide wire catheter extends through the lumen within the pusher catheter;
an access sheath disposed within each of the two side ports of the manifold; and
a sheath disposed coaxially over the pusher catheter having a distal end that is rotatably coupled to the handle, where the sheath has at least two longitudinal splits formed along the length of the sheath from the distal end of the sheath to the manifold, where each split is aligned with each of the access sheaths such that the sheath can be at least partially retracted over the access sheaths.

12. The pre-loaded stent graft delivery device of claim 11 where the handle assembly comprises threads about which the handle rotates.

13. The pre-loaded stent graft delivery device of claim 12 where the rotation of the handle in one direction retracts the sheath.

14. The pre-loaded stent graft delivery device of claim 13 wherein the pusher catheter further comprises two longitudinal auxiliary lumens.

15. A pre-loaded stent graft delivery device comprising:
a manifold with three access ports, three sheath apertures on a proximal end of the manifold, and a central aperture, the three access ports extending distally from the central aperture;
three access sheaths, where each access sheath is disposed within a corresponding access port of the manifold;
a tri-lumen catheter extending proximally from the manifold, the tri-lumen catheter comprising three auxiliary lumens therethrough where each access sheath extends through a corresponding auxiliary lumen within the tri-lumen catheter; and
a sheath disposed coaxially over the tri-lumen catheter, where the sheath has at least three longitudinal splits formed along a portion of the length of the sheath, where each split is aligned with a corresponding access sheath such that the sheath can be at least partially retracted over the access sheaths.

16. The pre-loaded stent graft delivery device of claim 15 further comprising a stent graft being releasably retained within each access sheath.

17. The pre-loaded stent graft delivery device of claim 16 further comprising three guide wires, where each guide wire is disposed within a corresponding access sheath.

18. The pre-loaded stent graft delivery device of claim 15, wherein each portion of the length of the sheath is aligned with a corresponding sheath aperture such that the portions of the length of the sheath can be at least partially retracted through the sheath apertures.

19. The pre-loaded stent graft delivery device of claim 15 further comprising a cutter connected to a proximal end of the manifold.

20. The pre-loaded stent graft delivery device of claim 19, wherein the cutter comprises a fixture, at least one blade housing connected to the fixture, and at least one blade connected to said at least one blade housing.

* * * * *